(12) United States Patent
Kostenich et al.

(10) Patent No.: US 12,262,993 B2
(45) Date of Patent: Apr. 1, 2025

(54) SYSTEM AND METHOD FOR DETERMINING OXYGENATED- BLOOD CONTENT OF BIOLOGICAL TISSUE

(71) Applicant: Tel Hashomer Medical Research Infrastructure and Services Ltd., Ramat Gan (IL)

(72) Inventors: Genady Kostenich, Bat Yam (IL); Arie Orenstein, Tel Aviv (IL); Mor Oron-Herman, Yehud (IL)

(73) Assignee: Tel Hashomer Medical Research Infrastructure and Services Ltd., Ramat Gan (IL)

( * ) Notice: Subject to any disclaimer, the term of this patent is extended or adjusted under 35 U.S.C. 154(b) by 1067 days.

(21) Appl. No.: 17/272,645

(22) PCT Filed: Aug. 27, 2019

(86) PCT No.: PCT/IL2019/050959
§ 371 (c)(1),
(2) Date: Mar. 1, 2021

(87) PCT Pub. No.: WO2020/044337
PCT Pub. Date: Mar. 5, 2020

(65) Prior Publication Data
US 2021/0338119 A1    Nov. 4, 2021

Related U.S. Application Data
(60) Provisional application No. 62/724,116, filed on Aug. 29, 2018.

(30) Foreign Application Priority Data
Dec. 4, 2018    (IL) ........................................... 263498

(51) Int. Cl.
*A61B 5/1455* (2006.01)
*A61B 5/00* (2006.01)

(52) U.S. Cl.
CPC ........ *A61B 5/14551* (2013.01); *A61B 5/0059* (2013.01); *A61B 2505/05* (2013.01)

(58) Field of Classification Search
CPC .......................... A61B 5/1455; A61B 5/14552
See application file for complete search history.

(56) References Cited

U.S. PATENT DOCUMENTS

| 2004/0116814 A1 | 6/2004 | Stranc et al. |
| 2005/0136195 A1 | 6/2005 | Raval |

(Continued)

FOREIGN PATENT DOCUMENTS

| CN | 104549162 A | 4/2015 |
| CN | 107822592 A | 3/2018 |

(Continued)

OTHER PUBLICATIONS

K. Banerjee-Ghosh et al "Separation of enantiomers by their enantiospecific interaction with achiral magnetic substrates", Science 360, pp. 1-4 (2018).

(Continued)

*Primary Examiner* — Marjan Fardanesh
(74) *Attorney, Agent, or Firm* — The Roy Gross Law Firm, LLC; Roy Gross

(57) ABSTRACT

Some embodiments are directed to a system and method monitoring oxygenation in biological tissue, comprising a control unit configured and operable to receive data indicative of light response from a region of the biological tissue being subjected to illumination and/or collection at two separate wavelengths in two selected wavelength ranges and processing the data by comparing data indicative of each selected wavelength range to determine an oxygenated/

(Continued)

deoxygenated status of the biological tissue. The two wavelength ranges include a first wavelength range in which the absorbance of the deoxyhemoglobin within the tissue is higher than the oxyhemoglobin, and a second wavelength range in which the absorbance of the oxyhemoglobin within the tissue is higher than the deoxyhemoglobin or vice versa. The two wavelengths in the two wavelength ranges include first and second wavelengths satisfying a predetermined condition of a ratio between the absorbance of the deoxyhemoglobin and oxyhemoglobin for each wavelength.

20 Claims, 17 Drawing Sheets
(13 of 17 Drawing Sheet(s) Filed in Color)

(56) References Cited

U.S. PATENT DOCUMENTS

| | | |
|---|---|---|
| 2013/0018242 A1 | 1/2013 | Yamaguchi et al. |
| 2014/0180129 A1 | 6/2014 | Kostenich et al. |
| 2015/0265195 A1 | 9/2015 | Darty et al. |
| 2016/0361003 A1 | 12/2016 | Lange et al. |
| 2017/0224260 A1 | 8/2017 | Darty et al. |

FOREIGN PATENT DOCUMENTS

| | | |
|---|---|---|
| DE | 19838606 A1 | 3/2000 |
| JP | H9508291 A | 8/1997 |
| JP | 2010522603 A | 7/2010 |
| JP | 2013017769 A | 1/2013 |
| JP | 2013544588 A | 12/2013 |
| JP | 2015501194 A | 1/2015 |
| JP | 2015092888 A | 5/2015 |
| JP | 2018051304 A | 4/2018 |
| WO | 9520757 A1 | 8/1995 |
| WO | WO2012/061584 A2 | 5/2012 |
| WO | 2017094010 A1 | 6/2017 |
| WO | 2019043693 A1 | 3/2019 |

OTHER PUBLICATIONS

Claudio Fontanesi et al: "Spin-Dependent Processes Measured without a Permanent Magnet", Advanced Materials, vol. 30, No. 41, May 7, 2018, pp. 1-6.
Wenyan Zhang et al: "Enhanced Electrochemical Water Splitting with Chiral Molecule-Coated Fe 3 0 4 Nanoparticles", ACS Energy Letters, vol. 3, No. 10, Oct. 12, 2018, pp. 1-16.
EPO extended European Search Report for EP19855346 dated Oct. 25, 2021.
International Search Report for PCT Patent App. No. PCT/IL2019/050959 dated Dec. 31, 2019.
The State Intellectual Property Office of the People's Republic of China, The First Office Action for Chinese Patent Application No. 201980072283.1, dated Mar. 8, 2024, 21pp.

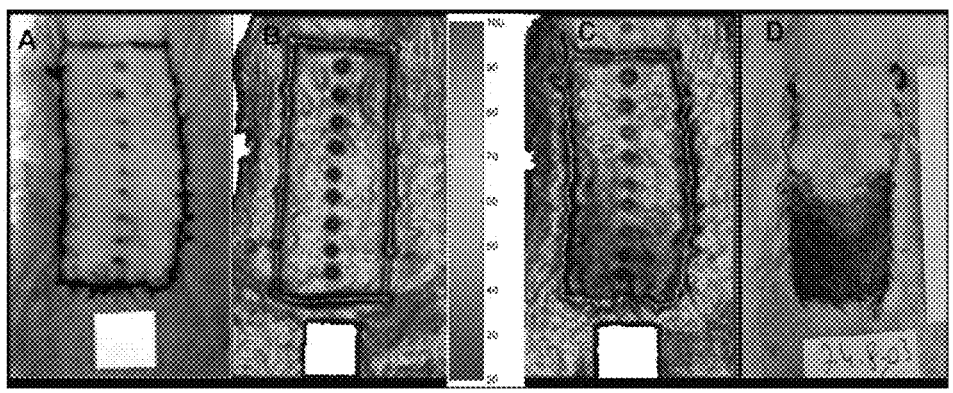
Figure 12A    Figure 12B    Figure 12C    Figure 12D
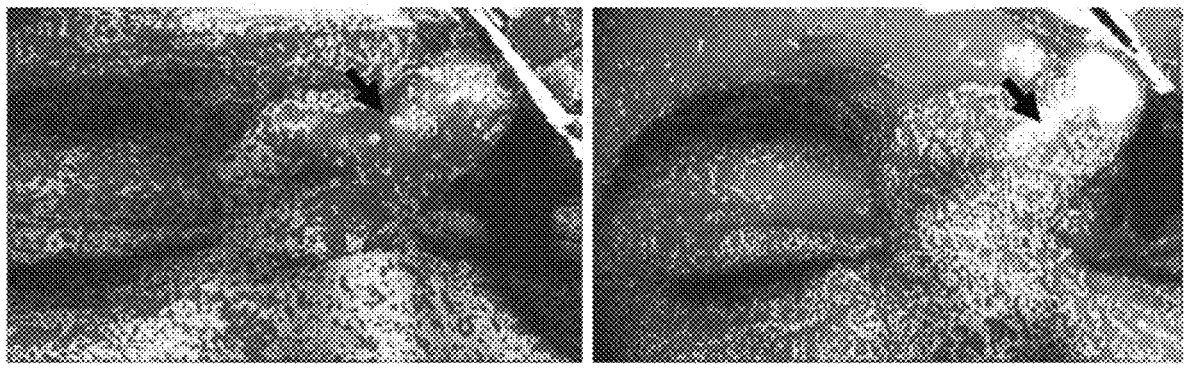
Figure 13A                    Figure 13B

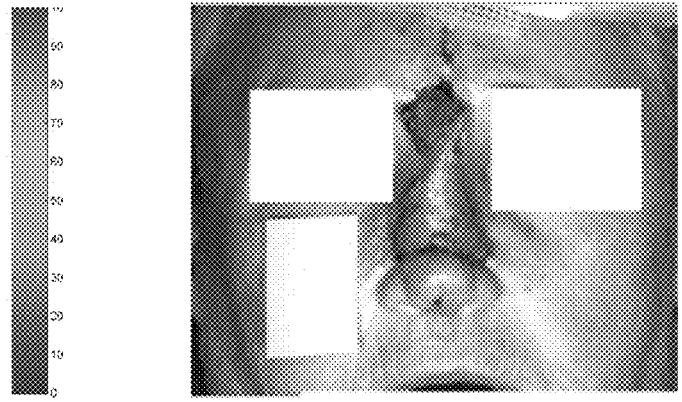
Figure 14A
Figure 14B
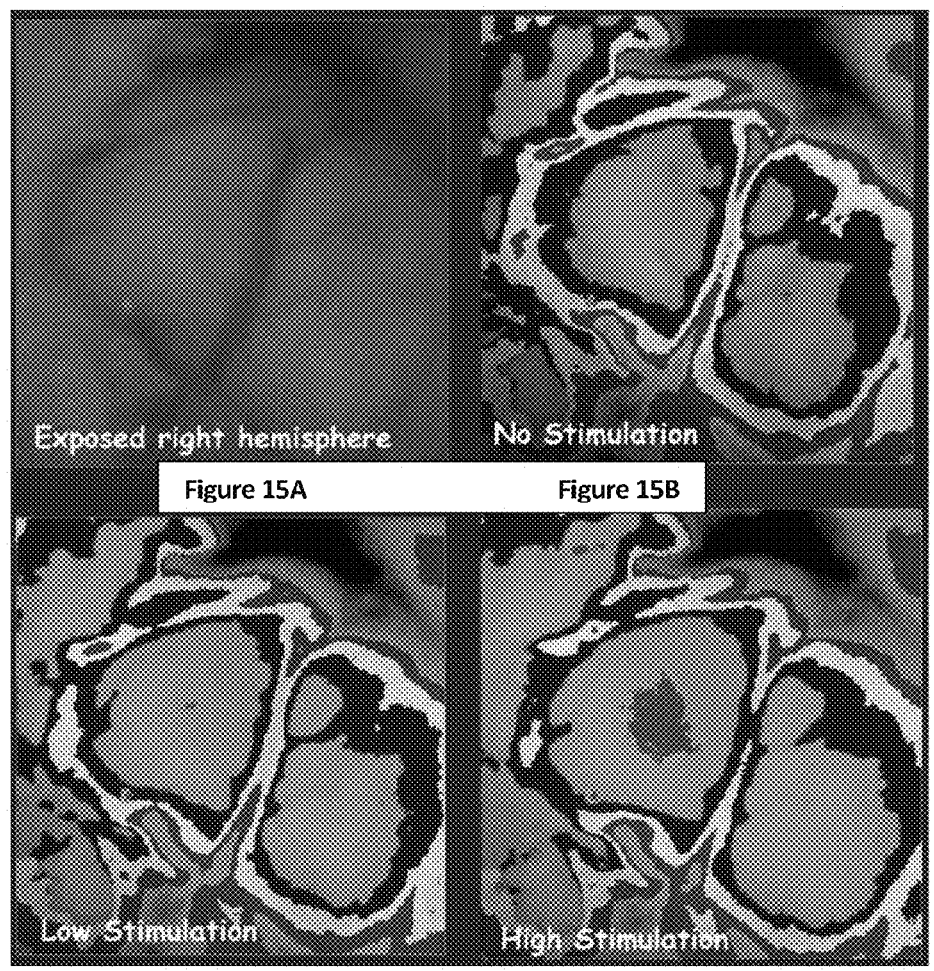
Figure 15C
Figure 15D

SYSTEM AND METHOD FOR DETERMINING OXYGENATED- BLOOD CONTENT OF BIOLOGICAL TISSUE

CROSS REFERENCE TO RELATED APPLICATION(S)

This application is a national phase filing under 35 C.F.R. § 371 of and claims priority to PCT Patent Application No. PCT/IL2019/050959, filed on Aug. 27, 2019, which claims the priority benefit under 35 U.S.C. § 119 of U.S. Provisional Application No. 62/724,116 and Israeli Patent Application No.: 263498, filed on Aug. 29, 2018 and Dec. 4, 2018, respectively, the contents of each of which are hereby incorporated by reference in their entireties.

BACKGROUND

Some embodiments relate to a technique for determining the oxygenated-blood content of biological tissue, and in particular to a technique for tissue oxygenation mapping.

Under various circumstances in the field of medicine it is useful to determine the content of oxygenated-blood in biological tissue. Regional oxygen transport has an important role in maintaining tissue function. Hypoxia in individual tissues or organs, associated with local disrupted microcirculation caused by capillary dysfunction, cannot be identified from global (systemic) measurements of peripheral oxygen saturation ($SpO_2$). Various chronic, as well as acute medical conditions, (e.g. peripheral vascular disease, diabetes mellitus, hypercholesterolemia, hypertension, chronic renal failure, chronic obstructive pulmonary disease, abdominal aortic aneurysmal disease, venous insufficiency, various kinds of surgery) are associated with impaired local tissue oxygenation.

For example, in plastic surgery, such as flap surgery, a portion of tissue is at least partially excised from blood vessels that are responsible for the flow of blood through the portion of tissue, the tissue is moved to a different new location of the body, and often connected to new blood vessels that are in proximity of the new location. If the connection to the new blood vessels is successful and, when present, the original connection to old blood vessels remains good and the healing process proceeds well, the portion of tissue receives an adequate supply of oxygenated blood from arteries, deoxygenated blood is carried away by veins, and the portion of tissue is viable. However, if some problem occurs and for some reason the portion of tissue has an insufficient oxygenated blood content, e.g., arteries do not supply enough oxygenated blood, or veins do not carry away enough deoxygenated blood so that the portion of tissue is not viable. If the fact that the portion of tissue does not contain enough oxygenated blood is detected soon enough, measures can be taken to save the portion of tissue. If the fact that the portion of tissue which does not contain enough oxygenated blood is not detected soon enough, necrosis occurs, and the portion of tissue must or should be excised.

For example, in emergency medicine, a person may arrive for medical care where widespread portions of the body are severely damaged, including partial amputation, so it is not possible for medical personnel to determine which portions of the body are viable, and which are not. To treat the person, it would be useful to be able to quickly determine which portions of the body have sufficient oxygenated-blood content to be viable, and which do not. Those portions of the body that are found to be viable can then be treated first to ensure survival, and for those portions which are not immediately viable, medical personnel can decide whether it is possible to reconnect blood supplies, or to excise those body parts, thereby increasing patient survival and recovery rates.

SUMMARY

There is a need in the related art to provide a non-invasive technique enabling identification of the above-mentioned dysfunctions to allow clinicians to identify those at increased risk for peripheral and cardiovascular diseases. It would also be useful to have a technique that is useful in determining, qualitatively and/or quantitatively, the oxygenated-blood content of tissue. To this end, the presently disclosed subject matter provides a novel technique for providing an indication on tissue oxygenation. More specifically, the system is configured for measuring biological tissue to determine the oxygenated/deoxygenated blood present in the tissue. The presently disclosed subject matter provides a technique for measuring oxygen saturation in tissue capillaries based on a spectral analysis of unique wavelengths that differentiate oxygenated hemoglobin from non-oxidized. The technique may serve as the basis for a variety of systems for diverse clinical uses.

According to a broad aspect of the presently disclosed subject matter, there is provided a system for monitoring oxygenation in biological tissue. The system includes a control unit being configured and operable to receive data being indicative of light response from the same region of the biological tissue being subjected to illumination and/or collection at two separate wavelengths in two selected wavelength ranges and processing the data by comparing data indicative of each selected wavelength range to determine an oxygenated/deoxygenated status of the biological tissue, wherein the two wavelength ranges of illumination and/or collection include a first wavelength range in which the absorbance of the deoxyhemoglobin within the tissue is higher than the oxyhemoglobin, and a second wavelength range in which the absorbance of the oxyhemoglobin within the tissue is higher than the deoxyhemoglobin or vice versa, and the two wavelengths in the two wavelength ranges include first and second wavelengths satisfying a predetermined condition for a ratio between the absorbance of the deoxyhemoglobin and the oxyhemoglobin for each of the first and second identified wavelengths.

Such predetermined condition corresponds to a relatively high ratio between the absorbance of the deoxyhemoglobin and the oxyhemoglobin for each of the first and second identified wavelengths. In this connection, it should be noted that the relatively high ratio between these absorbances, which is preferably substantially/approximately highest/maximal ratio, corresponds to the condition that absorbance properties (intensities) of the deoxyhemoglobin and oxyhemoglobin for each of these two wavelengths are significantly (maximally) different from one another.

In some embodiments, the first wavelength range is selected such that the data is indicative of a tissue portion located at the surface of the tissue region being monitored, while the second wavelength range is indicative of a tissue portion located in the depth of the tissue region. In this case, the first and second wavelength ranges are located in different spectral bands, being blue and red spectral bands. The first wavelength may be near/around 415 nm, in the first wavelength range from about 400 nm to about 420 nm and the second wavelength may be near/around 650 nm in the second wavelength range from about 600 nm to about 800 nm. In another possible example, the first wavelength is near/around 470 nm in the first wavelength range of 450-500 nm, and the second wavelength is near/around 650 nm in the second wavelength range of 600-800 nm.

In some other embodiments, which may be used alternatively to or additionally with the above described embodiments, the first and second wavelength ranges are substantially in the same spectral band, and the first and second wavelength ranges are selected such that the measured data is indicative of a surface tissue portion of the tissue region being monitored. The first wavelength may be near/around approximately 415 nm in the first wavelength range of 400-420 nm, and the second wavelength may be near/around approximately 435 nm in the second wavelength range of 420-450 nm. Another possible example for these embodiments is the use of the first wavelength near 435 nm of the first wavelength range of 420-450 nm, and the second wavelength near 470 nm of the wavelength range of 450-500 nm.

In some embodiments, the control unit is configured and operable to process the data by calculating a relation (e.g. ratio) between two averaged intensities being indicative of the light response from the same region of a biological tissue being illuminated and/or collected at the two separate selected wavelength ranges. This relation is indicative of/describes the oxygenated/deoxygenated status of the biological tissue. It should be understood that such relation (ratio) between the measured light responses for the selected wavelengths might be of a certain normal value, which may be individual specific and/or measurement location (body portion) specific. This normal value might be determined in a calibration or preliminary machine learning procedure. Thus, what is actually to be measured/detected is a change of the relation (ratio) from the normal value.

In some embodiments, the control unit is configured and operable to determine the oxygenated/deoxygenated status of the biological tissue in real-time.

In some embodiments, tissue is illuminated by using two electromagnetic beams having different wavelength ranges (e.g. blue and red wavelength ranges). Two reflected back-scattered light beams corresponding to the different wavelength ranges are then collected by using a detector unit (imaging or non-imaging). The system may include an imager unit being configured and operable to receive the light response and to generate at least two pixelated images thereof.

As used herein, the term "imager unit" refers to any device capable of generating a digital pixelated image data (as stills or video). The data may include at least two pixelated images. As used herein, for clarity the term "image" refers to a visible image (e.g., as displayed on permanent media such as on printed paper or electronic media such as a display screen (LED, LCD, CRT)), as well as image data (especially electronic data) representing the image including data stored, for example, on magnetic or electrical media (e.g., flash memory, magnetic disk, magnetic tape).

The processing of the data may include identifying in each image, pixels being indicative of a specific area of the region; performing pixel-by-pixel comparison of the at least two pixelated images for each specific area; determining an oxygenated/deoxygenated-tissue status of the biological tissue per pixel, and generating a processed image as map being indicative of a tissue oxygenation/deoxygenation status. As used herein, for clarity the term "pixel" refers to an element making up a pixelated image (displayed or stored as data) and also to the value of the pixel, as the context dictates. The control unit may be configured and operable to generate a processed image of the tissue region being indicative of oxygenation status of the tissue portion at the surface of the tissue in comparison with oxygenation status of tissue portion in the depth of the tissue.

If an imager unit is used, the image data being indicative of the two reflected back-scattered light beams is thus compared pixel per pixel to determine the oxygenated/deoxygenated blood present in the tissue. An image may be then obtained by performing pixel-by-pixel comparison of the first and the second image data to generate blood-oxygenation tissue status map data. A full color mapping is performed by extracting selected appropriate wavelength ranges.

In some embodiments, the imager unit includes a spectral imager being configured and operable to receive the light response and to generate at least two pixelated spectral images thereof. The data may thus include at least two pixelated spectral images. The processing of the data may include extracting from the at least two pixelated spectral images, at least two monochrome images corresponding to the selected wavelength ranges of illumination and/or collection respectively, performing pixel-by-pixel comparison for each specific area of the at least two monochrome images and generating a processed image being indicative of a spectrally-resolved tissue oxygenation/deoxygenation mapping.

In some embodiments, the imager unit includes at least two imagers, each imager being configured and operable to detect at least one electromagnetic beam in a different selected wavelength range.

In some embodiments, the system includes at least two cross polarizing elements being associated with an illumination source and the imager unit and being configured and operable to filter out specular reflection from the tissue.

In some embodiments, the system includes a non-imaging photodetector unit which is configured and operable to acquire non-image data. The non-imaging photodetector unit can be configured and operable to receive the light response of the same region from a biological tissue being illuminated and/or collected at the two separate selected wavelength ranges and to generate at least two averaged intensities of the region thereof. The data may thus include non-imaging data being indicative of at least two averaged intensities at the two separated wavelengths ranges. The processing of the data may include calculating a ratio between the two averaged intensities. Any suitable detector unit or combination of detectors may be used to determine the intensity of the light response (e.g. diffusely-reflected light). For example, a detector unit including optoelectronic components may be used such as photoelectric light detectors (e.g., photodiodes, phototransistors, photomultipliers, optiosolators, and integrated optical circuits), photoconductivity detectors (e.g., photoresistors, photoconductive camera tubes, charge-coupled devices), stimulated emission detectors (e.g., injection laser diodes, quantum cascade lasers), radiative recombination detectors (light-emitting diodes, organic light-emitting diodes) and photoemissitivy detectors (photoemissive camera tubes).

In some embodiments, the system includes an illumination source being configured and operable to illuminate biological tissue with two separate wavelength ranges of electromagnetic beams.

In some embodiments, the technique allows quantification and monitoring of treatment designed to prevent or improve microcirculatory function. In addition, assessment of microcirculation functionality, and monitoring of local tissue oxygenation, both assist various surgical procedures (e.g. plastic surgery, tissue transplantations) in order to identify tissue vitality and for determining treatment endpoints and post-treatment tissue viability. In this connection, it should be understood that assessment of regional tissue oxygenation can be a great challenge, since global hemodynamic variables provide only a rough estimation of organ perfusion. The systemic parameter of SpO2 is insensitive and a nonspecific indicator of safe oxygenation at the regional tissue level.

The surface of biological tissue is any suitable surface. In some embodiments, the region of biological tissue may be a two dimensional matrix overlayed on the surface of biological tissue. In some embodiments, the surface is skin, especially human skin. In some embodiments, the surface is an inner surface of an intestinal tract. In some embodiments the surface is neural tissue of the brain. In some embodiments the surface is the dura mater covering the brain. In some embodiments the surface is muscle tissue. In some embodiments the surface is the surface of the retina that faces the inside of an eyeball.

According to another broad aspect of the presently disclosed subject matter, there is provided a method for use in monitoring oxygenation in biological tissue. The method includes determining operational data for use in one or more measurement sessions to enable collection of data indicative of oxygenated/deoxygenated tissue status of the biological tissue, the determining including selecting two separate wavelengths in two wavelength ranges for use in the one or more measurement sessions (for illumination and/or collection of light response) to enable generation of data indicative of light response of a region of the biological tissue to the two wavelengths. The two wavelength ranges can be selected by identifying a first wavelength range in which the absorbance of the deoxyhemoglobin within the tissue is higher than the oxyhemoglobin, and a second wavelength range in which the absorbance of the oxyhemoglobin within the tissue is higher than the deoxyhemoglobin, or vice versa, and selecting first and second wavelengths from the first and second wavelength ranges, satisfying a condition of a relatively high (preferably highest) ratio between the absorbance of the deoxyhemoglobin and the oxyhemoglobin for each of the identified wavelengths.

The method may further include analysis of measured data obtained in the one or more measurement sessions using the above operational data, the measured data being indicative of a light response from the same region of biological tissue at the above-described two separate selected wavelength ranges; and determination of an oxygenated/deoxygenated status of the biological tissue.

In some embodiments, the method includes implementing the one or more measurement session while reducing specular reflection from the tissue.

In some embodiments, the method includes illuminating biological tissue with at least two electromagnetic beams having different selected wavelength ranges.

In some embodiments, the method includes collecting imaging or non-imaging data being indicative a light response from the same region of biological tissue at two separate selected wavelength ranges.

In some embodiments, the method includes displaying an oxygenation/deoxygenation tissue status of the region of interest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to better understand the subject matter that is disclosed herein and to exemplify how it may be carried out in practice, embodiments will now be described, by way of non-limiting example only, with reference to the accompanying drawings, in which:

FIG. 2C shows raw data of the measured light response for the two wavelengths λ1 and λ2 measured on human arm at normal condition (i.e. no blood vessels occlusion), FIG. 2D shows the respective light responses measured on the human arm at the start of the occlusion mode, and FIG. 2E shows the evolution of the respective light responses during the 2 min period of the occlusion mode;

FIGS. 12A-12D show the teachings herein used for determining the oxygenation of a transplanted skin flap on a mouse;

FIGS. 13A-13B show the teachings herein used for determining the oxygenation of a skin flap produced by a forehead to nose transposition;

FIGS. 14A-14B show the teachings herein used for determining the oxygenation of tissue during nose reconstruction;

FIGS. 15A-15D show the teachings herein used for real-time monitoring of brain function;

DETAILED DESCRIPTION OF EXEMPLARY EMBODIMENTS

Unless otherwise defined, all technical and scientific terms used herein have the same meaning as commonly understood by one of ordinary skill in the art to which some embodiments of the presently disclosed subject matter pertains. In case of conflict, the specification, including definitions, will take precedence.

As used herein, the terms "including", "having" and grammatical variants thereof are to be taken as specifying the stated features, integers, steps or components, but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, a phrase in the form "A and/or B" means a selection from the group consisting of (A), (B) or (A and B). As used herein, a phrase in the form "at least one of A, B and C" means a selection from the group consisting of (A), (B), (C), (A and B), (A and C), (B and C) or (A and B and C).

Embodiments of methods and/or systems described herein may involve performing or completing selected tasks manually, automatically, or a combination thereof. Some methods and/or systems described herein are implemented with the use of components that include hardware, software, firmware or combinations thereof. In some embodiments, some components are general-purpose components such as general purpose computers, digital processors or oscilloscopes. In some embodiments, some components are dedicated or custom components such as circuits, integrated circuits or software.

It is appreciated that certain features of some embodiments of the presently disclosed subject matter, which are, for clarity, described in the context of separate embodiments, may also be provided in combination in a single embodiment. Conversely, various features of some embodiments of the presently disclosed subject matter, which are, for brevity, described in the context of a single embodiment, may also be provided separately or in any suitable subcombination, or, as suitable, in any other described embodiment of the presently disclosed subject matter. Certain features described in the context of various embodiments are not to be considered essential features of those embodiments, unless the embodiment is inoperative without those elements.

Figure 1:
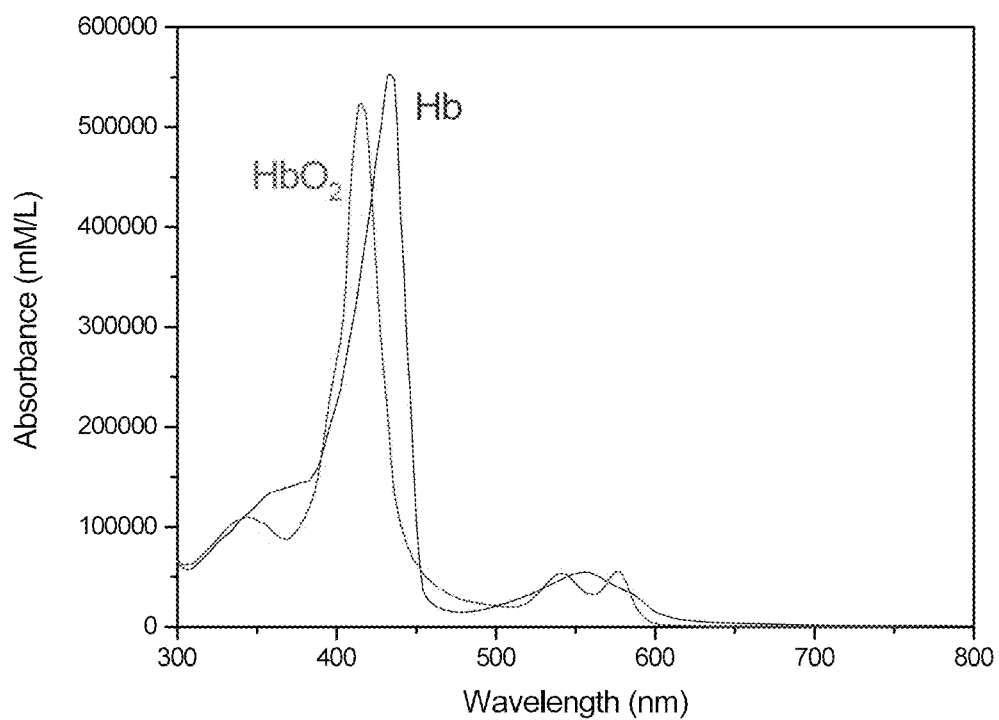
FIG. 1 shows a typical absorption spectra of Hemoglobin (Hb) and oxyhemoglobin ($HbO_2$)

Reference is made to FIG. 1, showing typical absorbance spectra of oxyhemoglobin ($HbO_2$) and (deoxy)hemoglobin (Hb). The applicant have found that by selecting two different wavelengths, and in some embodiments two wavelengths of different wavelength ranges, of illumination and/or collection such that a first wavelength in which the absorbance of the deoxyhemoglobin within the tissue is higher than the oxyhemoglobin, and a second wavelength in which the absorbance of the oxyhemoglobin within the tissue is higher than the deoxyhemoglobin, or vice versa, and the two wavelengths include first and second wavelengths satisfying a condition of a relatively high (substantially/approximately highest) ratio between the absorbance of the deoxyhemoglobin and the oxyhemoglobin for each of the first and second identified wavelengths, a special contrast is created. This unique selection of two different wavelengths provides the ability to detect a change between the absorbance of oxyhemoglobin ($HbO_2$) and (deoxy)hemoglobin (Hb). Importantly, this unique selection of two different wavelengths provides the ability to determine biological tissue status and to determine changes in the biological tissue status.

It should be understood that this approach is completely different from the pulse oxymetry approach in which $StO_2$ hemoglobin measurements are dependent on heart pulse signal. This special contrast enables to acquire data being indicative of surface tissue portion(s) of the tissue being monitored, and in some embodiments of data indicative of a first tissue portion located at the surface of the tissue being monitored and data indicative of a second tissue portion located in the depth of the tissue being monitored.

It should also be noted that the technique of some embodiments advantageously does not require any use of fluorescent techniques (which are costly, require to inject to the patient a substance which may be allergenic, and is time-consuming), as well as does not require injection of any substances to the patient (e.g. contrast agent) which may be allergenic.

Thus, this novel technique of some embodiments provides a tissue-oxygenation map without injecting any substance to the patient. The image clearly differentiates between arteries and veins. For example, pixels having the higher amount of oxygenated-blood (Ioxy) values are associated with the identified arteries. They can be displayed as red (qualitatively indicating more oxygenated blood in the tissue underlying the surface corresponding to that pixel). Pixels having intermediate Ioxy values associated with the identified veins may be displayed as blue (qualitatively indicating less oxygenated blood in the tissue underlying the retinal surface corresponding to that pixel). Pixels having low Ioxy values associated with the identified nervous and connective tissue devoid of blood may be displayed as white (qualitatively indicating the lack of any blood in the tissue underlying the retinal surface corresponding to that pixel).

Thus, in some embodiments, the first wavelength range is selected such that the data is indicative of tissue status at a tissue portion in the vicinity of the surface of the biological tissue, while the second wavelength range provides data indicative of tissue status at a tissue portion in the depth of the biological tissue being monitored. By using this novel technique there is provided an indication of tissue status, indicating whether the volume of biological tissue includes sufficient/insufficient oxygenated blood to be considered viable. Moreover, this technique provides a prediction tool enabling to assess tissue viability in transplantation.

For example, according to the principles described above, the lower range of the first wavelength (of the blue light) may be 400 nm or 405 nm or 410 nm or 412 nm. The upper range of the first wavelength may be 418 nm or 420 nm. Alternatively, the lower range of the first wavelength (of the blue light) may be 450 nm or 460 nm, or 465 nm or 468 nm.

The upper range of the first wavelength may be 472 nm or 475 nm or 480 nm or 500 nm.

For example, according to the principles described above, the lower range of the second wavelength (of the red light) may be 600 nm or 630 nm or 640 nm. The upper range of the first wavelength may be 660 nm or 670 nm or 800 nm.

In a specific and non-limiting example, the first and second wavelengths are specified as 415 nm and 650 nm (narrow and specific, not a broad range), where ratio between oxygenated and deoxygenated Hb is maximal.

The oxygenated-blood content in the volume of biological tissue underlying the area may be determined qualitatively. It may be qualified as sufficient oxygenated blood if it is relatively high (there is a large proportion of oxygenated blood) or insufficient oxygenated blood if it is relatively low (there is a small proportion of oxygenated blood). Hereinafter, the intensity (per pixel or averaged over the measured region) of the light response (i.e. back-scattered) from at least one area of the surface of the biological tissue of interest when illuminated and/or collected by a first range of wavelengths, is referred to as "Ifirst". As defined hereinabove, the term "Ifirst" as used herein is a determined intensity of light diffusely reflected (scattered) from at least one area of a surface of biological tissue in a first range of wavelengths (e.g. blue light) as a result of illuminating the at least one area with light having wavelengths in the first range of wavelengths, the first range of wavelengths as defined above. The intensity (per pixel or averaged over the measured region) of the light diffusely reflected (i.e. back-scattered) from the same area of the surface of the biological tissue of interest when illuminated and/or collected by a second range of wavelengths is referred to as "Isecond". As defined hereinabove, the term "Isecond" as used herein is a determined intensity of light diffusely reflected from at least one area of a surface of biological tissue in a second range of wavelengths (e.g. red light) as a result of illuminating the at least one area with light having wavelengths in the second range of wavelengths, the second range of wavelengths as defined above. It has been found that a higher Isecond, accompanied by a lower Ifirst, indicates that a volume of biological tissue underlying an area of a surface of biological tissue contains relatively more oxygenated blood, while a lower Isecond accompanied by a higher Ifirst indicates that a volume of biological tissue underlying the area contains comparatively less oxygenated blood.

In this connection, reference is made to FIGS. 2A to 2E illustrating a specific and non-limiting example of measuring the changes in intensity of two preselected wavelengths as a function of time before and during blood flow occlusion procedure using a photodetector/oscilloscope device.

Figure 2A:
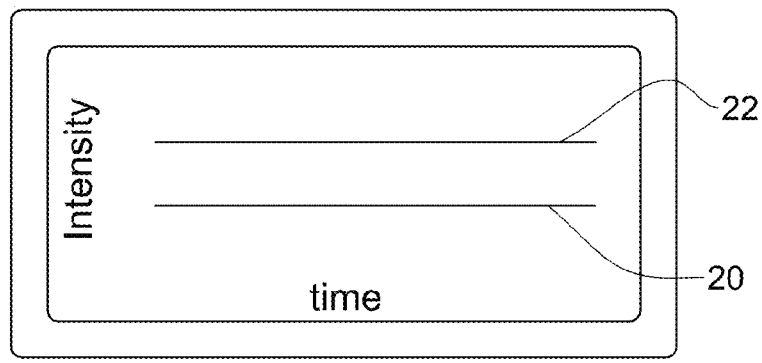
FIGS. 2A and 2B schematically depict a display screen of light detection device (photodetector, oscilloscope) used for measuring the changes in intensity of two preselected wavelengths as a function of time before and during blood flow occlusion procedure.
Figure 2B:
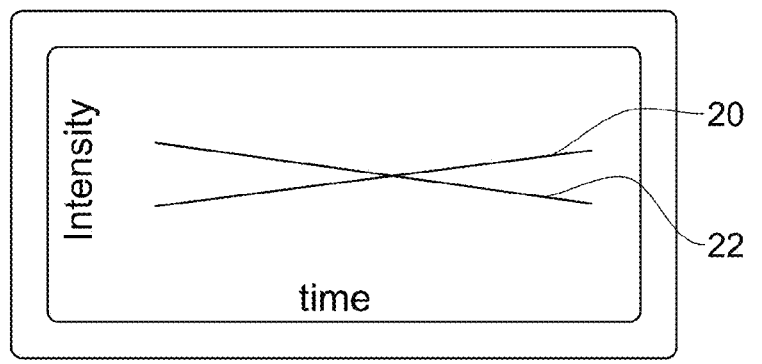

In FIGS. 2A and 2B, traces 20 and 22 correspond to the time evolution of the measured signals (light response intensity) for first and second wavelengths.

Figure 2C:
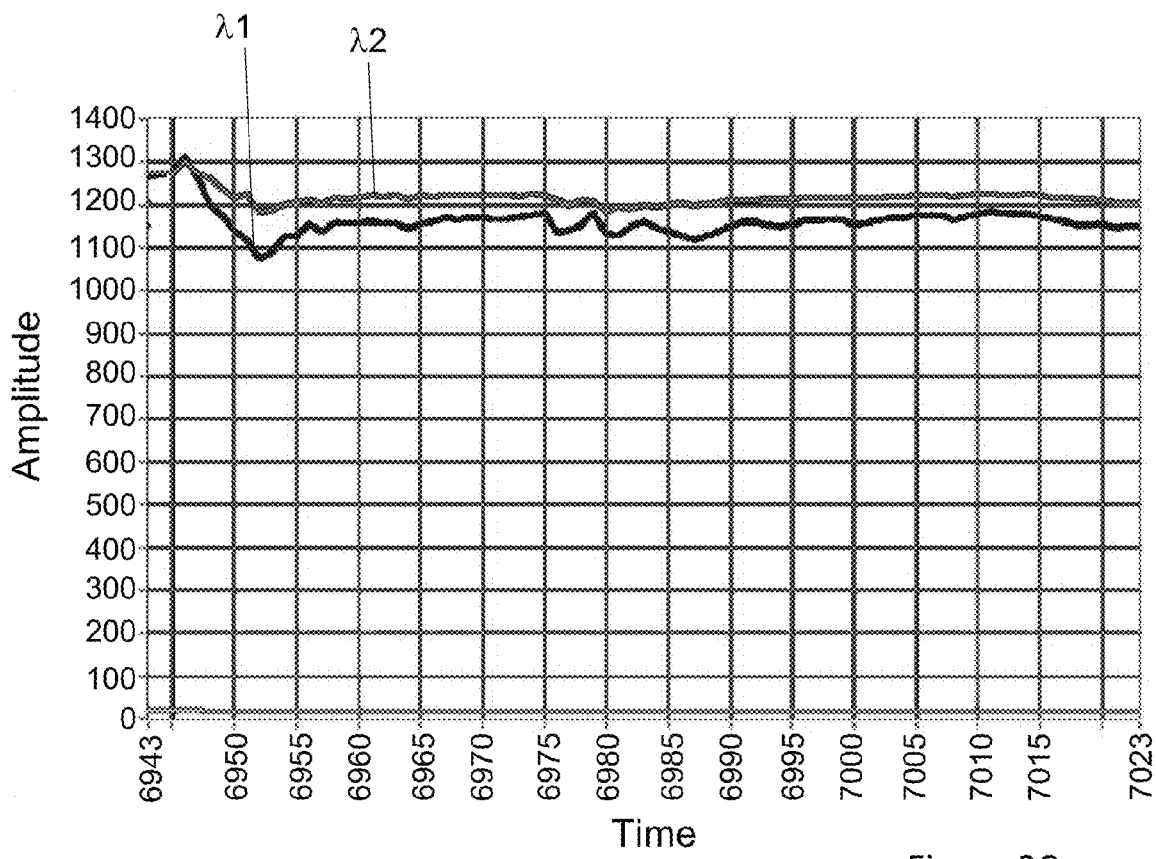
FIGS. 2C to 2E show more specifically the experimental results, where
Figure 2D:
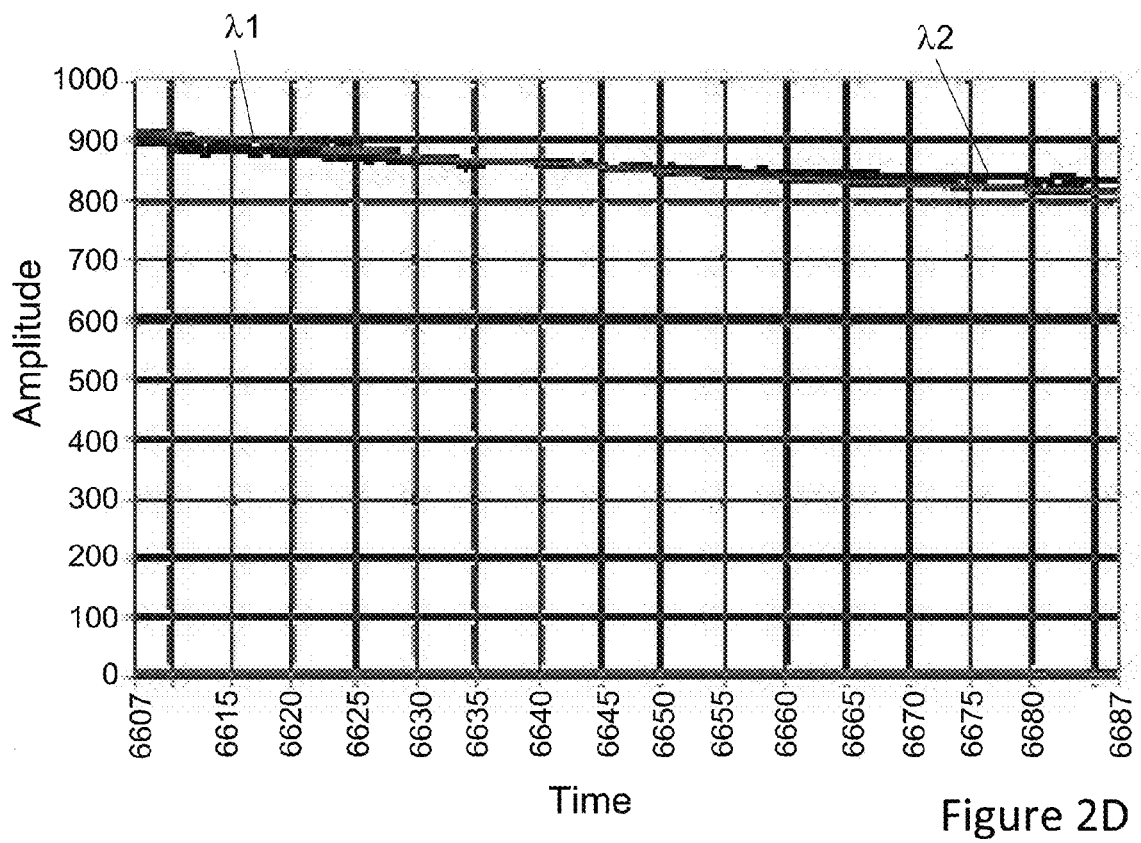
Figure 2E:
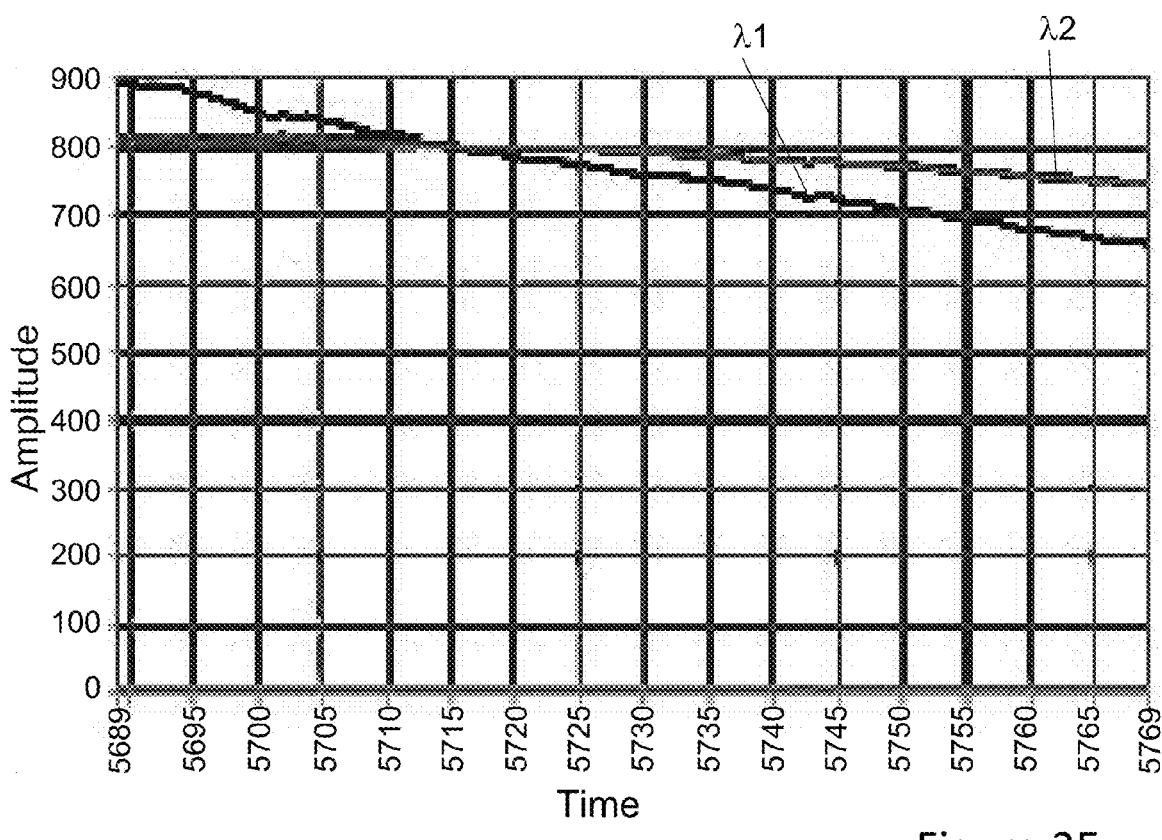

FIGS. 2C to 2E show more specifically raw data of the measured light response for the two wavelengths λ1 and λ2 measured on human arm at normal condition, i.e. no blood vessels occlusion (FIG. 2C), the respective light responses measured on the human arm at the start of the occlusion mode (FIG. 2D), and the evolution of the respective light responses during the 2 min period of the occlusion mode (FIG. 2E).

In this non-limiting example, both Ifirst and Isecond are repeatedly determined using one or more photodetectors (e.g., at 60 Hz) and input to the oscilloscope which displays the values of Ifirst and Isecond as a function of time as traces on an oscilloscope screen. External signal amplifiers or amplifiers may be a part of the oscilloscope and may be used to ensure that both Ifirst trace 20 and Isecond trace 22 are simultaneously displayed on the oscilloscope screen at a similar value allowing comparison.

As long as the distance (difference along the y-axis) between traces 20 and 22 of Ifirst and Isecond remain substantially constant as in FIG. 2A, the comparing provides evidence that supports a conclusion that the volume of biological tissue underlying the area of the surface of the biological tissue includes sufficient oxygenated blood (e.g. healthy) to be considered viable. If it is noted that the intensity value of trace 22 of Isecond becomes progressively lower while the intensity value of trace 20 of Ifirst becomes progressively higher as in FIG. 2B, the comparing provides evidence that supports a conclusion that the volume of biological tissue underlying the area of the surface of the biological tissue includes insufficient oxygenated blood (e.g. pre-necrotic or necrotic) to be considered viable.

For example, when monitoring the oxygenated blood content of tissue over time using a blood oxygenation monitor that includes a comparator for performing the comparing, both Isecond and Ifirst are repeatedly determined using one or more photodetectors (e.g., at 1 Hz). As long as the value of Isecond>Ifirst, the comparator outputs an indication that the comparing provides evidence that supports a conclusion that the volume of biological tissue underlying the area of the surface of the biological tissue includes sufficient oxygenated blood to be considered viable. If the value of Isecond<Ifirst, the comparator outputs an indication that the comparing provides evidence that supports a conclusion that the volume of biological tissue underlying the area of the surface of the biological tissue includes sufficient oxygenated blood to be considered viable, thus providing tissue status indication enabling monitoring of oxygenation in biological tissue.

Figure 3:
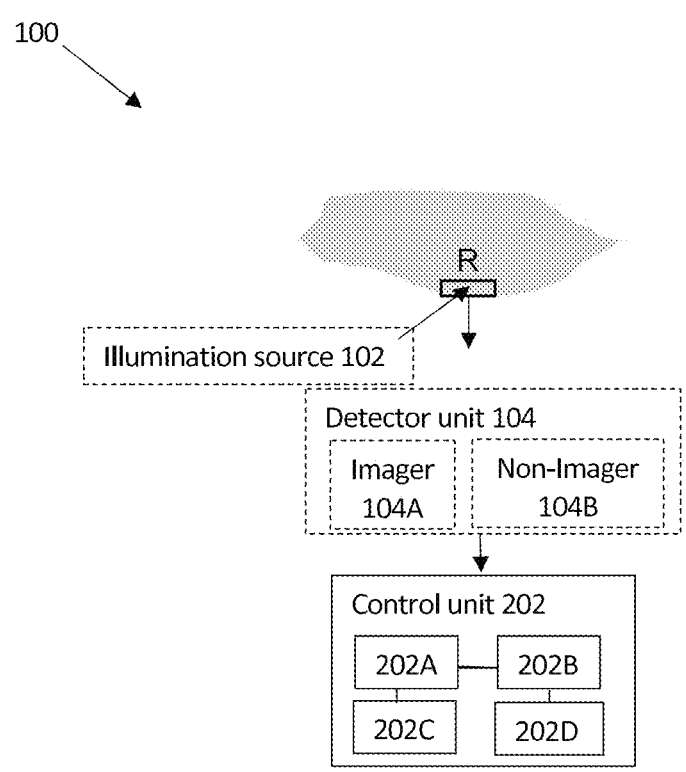
FIG. 3 is a block diagram illustrating an example of a system for data processing (control unit) providing monitoring of the oxygenation status of biological tissue

Reference is made to FIG. 3, showing a block diagram illustrating the main element of the system of the presently disclosed subject matter. System 100 is aimed at monitoring oxygenation in biological tissue. System 100 includes a control unit 202 being configured and operable to receive data being indicative of light response from the same region R of a biological tissue being subjected to illumination and/or collection of at least two separate wavelengths $\lambda_1$ and $\lambda_2$ in two selected wavelength ranges, and processes the data by comparing data indicative of each selected wavelength range to determine an oxygenated/deoxygenated status of the biological tissue. The two wavelength ranges of illumination and/or collection include a first wavelength range $\lambda_1$ in which the absorbance of the deoxyhemoglobin within the tissue is higher than the oxyhemoglobin and a second wavelength range $\lambda_2$ in which the absorbance of the oxyhemoglobin within the tissue is higher than the deoxyhemoglobin, or vice versa, and the two wavelengths in the two wavelength ranges include first and second wavelengths, each satisfying a condition of a relatively high ratio (preferably the highest/maximal or substantially/approximately highest/maximal ratio) between the absorbance of this wavelength by the deoxyhemoglobin and the oxyhemoglobin. In some embodiments according to the technique of some embodiments wherein appropriate selection of the first and second wavelengths penetrating at different depths within the tissue, control unit 202 is configured and operable to generate a processed image of the tissue being indicative of oxygenation status at the vicinity of the surface of the tissue in comparison with oxygenation status in the depth of the tissue.

In some embodiments, the oxygenated-blood status in the volume of the biological tissue underlying the area is determined quantitatively. It has been found that it is possible that Ifirst and Isecond for given tissue can together be correlated with numerical values of tissue oxygenation. As will be described below, the comparison of Ifirst to Isecond may yield a numerical value.

In some embodiments, control unit 202 is configured and operable to process the data by calculating a ratio between two averaged intensities being indicative of the light response from the same region of biological tissue being illuminated and/or collected at the two separate selected wavelength ranges.

For example, the status of the tissue may be calculated as follows:

$$Ioxy1 = \frac{(xIsecond + m)^A}{(yIfirst + n)^B}$$

and $$Ioxy2 = \frac{(yIfirst + n)^B}{(xIsecond + m)^A}$$

wherein A and B are, independently, any suitable positive number except 0 and including 1; wherein x and y are, independently, any suitable number including 1; and wherein m and n are, independently, any suitable number including 0.

For example the status of the tissue may be calculated as follows:

$$Ioxy1 = \frac{Isecond}{Ifirst} \text{ and } Ioxy2 = \frac{Ifirst}{Isecond}$$

In some embodiments, control unit 202 includes a computer processor for performing the comparison, for example, a computer processor such as found in processor devices such as desktop computers, laptop computers, hand-held computers, tablets, smartphones, digital cameras, medical device controllers and the like. As used herein, a computer processor can be an electronic device that can be programmed to perform mathematical functions and data processing. As used herein, a processor can be an electronic device that is configured for receiving as input two electronic signals and subsequently outputting an electronic signal that constitutes a comparison of the two electronic signals. Non-limiting examples of the term processor include comparators, division circuits, oscilloscopes and computer processors. Non-limiting examples of the term processor include microprocessors, digital processors (DSP), microcontrollers, field programmable gate arrays (FGPA), application specific integrated circuits (ASIC) as well as devices such as computers, personal computers, servers, smart phones and tablets. For implementing the teachings herein, such computer processors are typically programmed, e.g., through the use of software instructions, to carry out the functions and methods described herein.

Control unit 202 may be a part of a digital video camera or a part of a blood-oxygenation monitor. In some embodiments where control unit 202 is a part of a digital video camera, the system of the presently disclosed subject matter thereby displays a series of images as a video of real time blood-oxygenation of tissue underlying the surface of biological tissue, the output being a blood-oxygenation tissue status map. In some embodiments where the system is a blood-oxygenation tissue status monitor, control unit 202 may provide evidence that the flap has sufficient oxygenated blood content to be considered viable and outputs a different "warning" signal when the flap has insufficient oxygenated blood content to be considered viable.

In some embodiments, control unit 202 does not include a computer processor for performing the comparison, but includes a different processor suitable for performing the comparison, for example, an oscilloscope, a digital comparator and an analogue comparator, a digital division circuit, and an analogue division circuit.

Control unit 202 is in data communication with a detector unit 104 (e.g. optoelectronic component, digital camera) directly or indirectly (e.g. detector unit 104 acquires the data and stores the data on a storage component, then the data is recovered from the storage component and provided to control unit 202). If the detector unit 204 is placed at a certain distance from the object, the raw data received by control unit 202 may be, for example, intensity of numerous pixels at the different wavelengths of interest in a large area of interest. If the detector unit 204 is placed in contact with the object, the collected raw data may be the intensity at the different wavelengths of interest for a smallest area. If a regular imager unit 104A (being configured and operable to receive the light response and to generate at least two pixelated images thereof) is used, once the imaging unit collects the image data, the control unit 202 may perform pixel-by-pixel comparison of the at least two images, determine an oxygenated/deoxygenated status of the biological tissue per pixel, and generate a processed image being indicative of a tissue oxygenation/deoxygenation mapping. If a spectral imager (being configured and operable to receive the light response and to generate at least two pixelated spectral images thereof) is used, once an imaging unit collects the image data, the control unit 202 may extract from the at least two pixelated images, monochrome image data corresponding to the wavelength ranges of illumination and/or collection respectively, perform pixel-by-pixel comparison of the at least two monochrome images, determine an oxygenated/deoxygenated status of the biological tissue per pixel, and generate a processed image being indicative of a spectrally resolved tissue oxygenation/deoxygenation mapping. As used herein, the term "monochrome image data" refers to digital data representing a pixelated image where the value of each pixel is a single intensity value representing only an amount of light, that is, it carries only intensity information. If a non-imaging photodetector unit 104B (being configured and operable to receive the light response and to generate at least two averaged intensities of the region thereof) is used, control unit 202 may receive from the photodetector unit first and second averaged intensities of light diffusely reflected from at least one region of a surface of biological tissue in a first and second range of wavelengths as a result of illuminating and/or collecting the at least one area with light having wavelengths in the first and range of wavelengths respectively.

In general, control unit 202 may be a processor, a controller, a microcontroller or any kind of integrated circuit. Control unit 202 is configured generally as a computing/electronic utility including inter alia such utilities as data input 202A and output modules/utilities 202B, memory 202C (i.e. non-volatile computer readable medium), and analyzer/data processing utility 202D. The utilities of the control unit 202 may thus be implemented by suitable circuitry and/or by software and/or hardware components including computer readable code configured for receiving data indicative of the at least two pixelated images of the same region of biological tissue and for processing the data to generate a processed image being indicative of a spectrally resolved tissue oxygenation/deoxygenation mapping. The features of the presently disclosed subject matter may include a general-purpose or special-purpose computer system including various computer hardware components. Features within the scope of the presently disclosed subject matter also include computer-readable media for carrying out or having computer-executable instructions, computer-readable instructions, or data structures stored thereon. Such computer-readable media may be any available media, which are accessible by a general-purpose or special-purpose computer system. By way of example, without limitation, such computer-readable media can include physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g. Internet.

In this description and in the following claims, a "control unit" is defined as one or more software modules, one or more hardware modules, or combinations thereof, which work together to perform operations on electronic data. For example, the definition of a control unit includes the hardware components of a personal computer, as well as software modules, such as the operating system of a personal computer. The physical layout of the modules is not relevant. A computer system may include one or more computers coupled via a computer network. Likewise, a computer system may include a single physical device where internal modules (such as a memory and processor) work together to perform operations on electronic data. Control unit 202 may include a processor embedded therein running a computer program, or attached thereto. The computer program product may be embodied in one or more computer readable medium(s) having computer readable program code embodied thereon. The computer readable medium may be a computer readable signal medium or a computer readable storage medium. Computer program code for carrying out operations for aspects of the presently disclosed subject matter may be written in any combination of one or more programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). These computer program instructions may be provided to the processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. The specified functions of the processor can be implemented by special purpose hardware-based systems that perform the specified functions or acts, or combinations of special purpose hardware and computer instructions. In some embodiments, implementation includes a user interface, generally including one or more of input devices (e.g., allowing input of commands and/or parameters) and output devices (e.g., allowing reporting parameters of operation and results).

For example, a table of correspondence between the intensities of the different wavelengths and the numerical values of tissue oxygenation may be stored in a database. Such a table may be stored in memory 202C. Alternatively, storage may be separate from the server(s) (e.g. SAN storage). If separate, the location(s) of the storage may be in one physical location, or in multiple locations and connected through any type of wired or wireless communication infrastructure. The database may rely on any kind of methodology or platform for storing digital data. The database may include for example, traditional SQL databases such as Oracle and MS SQL Server, file systems, Big Data, NoSQL, in-memory database appliances, parallel computing (e.g. Hadoop clusters), etc. If memory 202C is configured as the storage medium of the database, it may include any standard or proprietary storage medium, such as magnetic disks or tape, optical storage, semiconductor storage, etc.

In some embodiments the system 100 can be configured in a cloud-based configuration and/or utilizes Internet based computing so that parts of processing utility 202D, and/or memory 202C may reside in multiple distinct geographic locations. After the THz response signal(s) is/are received, the data processing utility 202D is enabled to process the signal(s). Results of the signal processing step may be displayed by a display component and/or stored in storage component and/or sent to a data communication unit via a transmission component, a signal-producing component and a combination thereof.

More specifically, the data output 202B of the control unit 202 may be outputted by using at least one of the following actions:
    displaying a representation of the result of the processing using a display component which produces a transient or permanent image (such as display screen, e.g., LED, CRT, LCD or a printer) in a way that can be seen by a human,
    storing the result on a storage component (e.g., on magnetic media such as a magnetic disk, flash memory, solid state memory, computer memory, laser disk, floppy disk, magnetic tape),
    transmitting the result to a remote device using a transmission component (e.g., wirelessly using a transmitter such as Wi-Fi or Bluetooth® transceiver, cellular telephony transmitter, modulated light transmitter, radio-frequency transmitter or wired to a remote device such as a computer, server, smartphone, telephone, tablet); and
    producing a signal indicative of the result that can be perceived by a human using a signal-producing component (e.g., a visible signal that can be seen by a human, an audible signal that can be heard by a human, a tangible signal that can be felt by a human to indicate all-clear when the processing provides evidence that supports a conclusion that the volume of biological tissue includes sufficient oxygenated blood and/or a warning signal when the processing provides evidence that supports a conclusion that the volume of biological tissue includes sufficient oxygenated blood).

Examples of such signals that can be perceived by a person can be one or more of: audible signal (i.e., perceived by hearing) e.g., a gentle tone when the processing provides evidence that supports a conclusion that the volume of biological tissue includes sufficient oxygenated blood and/or an alarming tone as a warning signal when the processing provides evidence that supports a conclusion that the volume of biological tissue includes insufficient oxygenated blood; visible signal (i.e., perceived by sight) e.g., a green light when the processing provides evidence that supports a conclusion that the volume of biological tissue includes sufficient oxygenated blood and/or a flashing red light when the processing provides evidence that supports a conclusion that the volume of biological tissue includes insufficient oxygenated blood); and a tangible signal (i.e., perceived by touch) e.g., a gentle vibration when the processing provides evidence that supports a conclusion that the volume of biological tissue includes sufficient oxygenated blood and/or strong and persistent vibration when the processing provides evidence that supports a conclusion that the volume of biological tissue includes insufficient oxygenated blood).

Each pixel of the image data corresponds to a specific area i of the region of the surface of biological tissue. In some embodiments, control unit 202 identifies a specific area i in each image. More specifically, control unit 202 is configured to identify a corresponding pixel P1(i) in the first image data and a corresponding pixel P2(i) in the second image data. Control unit 202 then compares the value of P1(i) to the value of P2(i) to calculate a value Ioxy for pixel P3(i) in the blood-oxygenation tissue status map data corresponding to the location i. The resulting blood-oxygenation tissue status map data is a pixelated representation of the distribution of oxygenated-blood status in the tissue underlying the surface of the biological tissue.

In some embodiments, the blood-oxygenation tissue status map data is displayed as a visible single color monochrome image, that is to say, the displayed blood-oxygenation tissue status map data includes a single color where each pixel has a different intensity or shade of the color, depending on the value Ioxy of that pixel. Typical such visible single-color images are greyscale (for example, black being the lowest pixel value, white being the highest pixel value, and shades of grey being intermediate values), sepia and green.

For example, in some embodiments when the results of the comparing include blood-oxygenation tissue status map data, the output component is configured to display an image visible to a human, where portions of tissue with a better oxygenated blood tissue status are displayed differently from portions of tissue with a worse oxygenated blood tissue status. For example, in some embodiments the processor and the output component are configured to make a particular output when a comparing provides evidence that supports a conclusion that a volume of biological tissue includes sufficient oxygenated blood to be considered viable, e.g., an all-clear signal.

In some embodiments, the blood-oxygenation tissue status map data is displayed as a visible colorized monochrome image. In such embodiments, each pixel has only a single intensity value Ioxy, but each such intensity value can be displayed as a combination of two or more colors. For example, in one such embodiment, each pixel of a blood-oxygenation tissue status map data having an intensity value Ioxy between 0 and 255 is displayed in a visible colorized monochrome image by a pixel having an intensity of red light Ireddisplay=Ioxy and an intensity of blue light Ibluedisplay=255-Ioxy.

In the displayed image of this exemplary embodiment, high intensity value pixels are displayed as red, low intensity value pixels are displayed as blue, and intermediate intensity values pixels are displayed as various shades of purple. For example, in a different such embodiment, each pixel of a blood-oxygenation tissue status map data having an intensity value Ioxy between 0 and 255 is displayed in a visible colorized monochrome image by a pixel where a value of Ioxy between 0 and 100 is an increasingly lighter shade of blue, between 101 and 149 is an increasingly lighter shade of green, and between 150 and 255 is an increasingly darker shade of red.

In some embodiments, one or more of the outputting of the results is performed in real time. For example, in some embodiments, displaying an image that is representative of the results of the processing on an electronic display screen is performed in real time, for example, to assist a surgeon during surgery on a patient, to determine the relative oxygenated blood content of different parts of the patient.

Additionally or alternatively, control unit 202 outputs the generated blood-oxygenation tissue status map data continuously: for instance, when a digital video camera is used to continuously acquire a series of image data from which the processor continuously generates a corresponding series of blood-oxygenation tissue status map data, the resulting series of blood-oxygenation tissue status map data may be displayed continuously on a screen, assisting a health care professional during surgery, e.g., brain surgery, to identify areas of the cerebral cortex that become active when a specific stimulus is given to a patient.

For example, in some embodiments, an all-clear or warning signal are produced immediately after the processing is carried out.

For example, in some embodiments control unit 202 may locally store the results in real time and/or wirelessly transmits the results for storage (e.g., in an electronic medical file) in real time and/or activates a warning (e.g., to a nurses' station) to indicate to medical personnel that there is evidence that the underlying tissue is not viable. In some embodiments, control unit 202 activates a signal in real time, warning medical personnel of the result. In some embodiments, a signal is not produced in real time. The blood-oxygenation tissue status map data stored on the storage component is thereby recoverable, inter alia, for transfer, storing, archiving, displaying, study and automated analysis. The storage component is any suitable data storage component. In some embodiments, the storage component is one or more storage components selected from the group consisting of an optical storage component (e.g., laser disk, CD, DVD), on a magnetic storage component (e.g., hard disk, flash memory, magnetic tape, floppy disk), on a magneto-optical storage component (e.g., minidisc) and on an electronic storage component (e.g., Flash memory, solid-state drive).

Memory 202C may include instructions executable by data processing utility 202D. The instructions may be operable to enable data processing utility 202D to receive the data being indicative of light response, to process the data, to determine an oxygenated/deoxygenated status of the biological tissue, and to output via the data output utility 202B a notification regarding the oxygenated/deoxygenated tissue status. The notification may be relayed, via wireless or wired connection, by an external unit to a central database.

In some embodiments, system 100 may include a detector unit 104. Detector unit 104 may be incorporated to or may be an integral part of one of the following devices: a probe for determining the oxygenation status of biological tissue, a device for performing angiography, a device for performing retinal angiography, a spectral imaging camera, a digital medical camera, an ingestible endoscope, an endoscope, an ophthalmoscope, a fundus camera, a flexible endoscope, an esophagogastroduodenoscope, an enteroscope, a cholangiopancreatoscope, a colonoscope, a sigmoidoscope, a rhinoscope, a bronchoscope, a cystoscope, a gynoscope, a hysteroscope, a falloposcope, an amnioscope, a gastroscope, an otoscope, a laparoscope, a panendoscope and a fetoscope. In this case, some embodiments provide imaging instruments with analytical software showing the ability of hemoglobin oxygenation mapping in large tissue areas distantly or in contact. In some embodiments, detector unit 104 determines the Ifirst and the Isecond. In some embodiments, the detector unit that determines the Ifirst and the detector unit that determines the Isecond are different detectors, each detector being configured and operable to detect at least one electromagnetic beam in a different selected wavelength range. In some embodiments, the respective detectors determine the Ifirst and Isecond simultaneously. In some embodiments, the respective detectors determine the Ifirst and Isecond non-simultaneously.

In some embodiments, the imager unit 104A is a camera configured and operable to acquire a pixelated monochrome image data of a surface of biological tissue. The camera may be a monochrome camera.

In some embodiments, system 100 includes an illumination source 102 being configured and operable to illuminate the biological tissue with the two separate wavelength ranges of electromagnetic beams. Illumination source 102 includes at least one light source illuminating, with coherent or incoherent light, light within a narrow range of wavelengths such as a LED, a laser or with a broadband light source (e.g. a xenon lamp) provided with an optical filter, configured to illuminate exclusively with light of a specific one of the two wavelength ranges. For example, illumination source 102 is configured to alternatingly illuminate a surface of biological tissue with either exclusively the first light having wavelengths in the first range, or exclusively the second light having wavelengths in the second range. Illumination source 102 can be a single physical unit or multiple physically-separated units where the multiple units may be operable, together or independently. Control unit 202 may be configured for providing power to and for activating the other components of system 100 in accordance with the teachings herein. More specifically, control unit 202 may be configured and operable to control (e.g. activate) illumination source 102 and to select the wavelength ranges of illumination.

In some embodiments, the diffusely reflected light (of one or both of the two wavelength ranges) is guided to the detector unit with a light/wave guide. For example, the at least one area of the surface of tissue is illuminated with light that is produced by an illumination source 102 and guided to proximity of the surface with a light guide. Alternatively, in some embodiments, the diffusely reflected light (of one or both of the two wavelength ranges) reaches the detector unit 104 without the use of a light guide. Illuminating the at least one area with light having wavelengths in the first range of wavelengths and with light having wavelengths in the second range of wavelength, may be simultaneous or not.

In some such embodiments, the system 100 further includes at least one optical filter (e.g. changeable) that in a first state allows transmission of exclusively the first wavelength to a detector unit during which state the detector unit is configured for determining the data exclusively of the first wavelength range, and in a second state allows transmission of exclusively the second wavelength range to the detector unit during which state the detector unit is configured for determining the data exclusively of the second light. In some such embodiments, the detector unit includes a first detector unit being configured to exclusively detect the first wavelength range, and a second detector unit being configured to exclusively detect the second wavelength range.

In some embodiments, system 100 includes components to ensure that only diffusely reflected light is detected by the light detectors, e.g., by preventing detection of specularly reflected light. Components for ensuring that only diffusely reflected light is detected are well-known to a person having ordinary skill in the art. In some embodiments, detector unit 104 is functionally associated with a polarization filter, for example, a polarization filter that is cross-polarized relative to a polarized illuminator. In some embodiments, system 100 includes at least two cross polarizing elements being associated with illumination source 102 and the detector unit 104 and being configured and operable to filter out specular reflection from the tissue.

Figure 4:
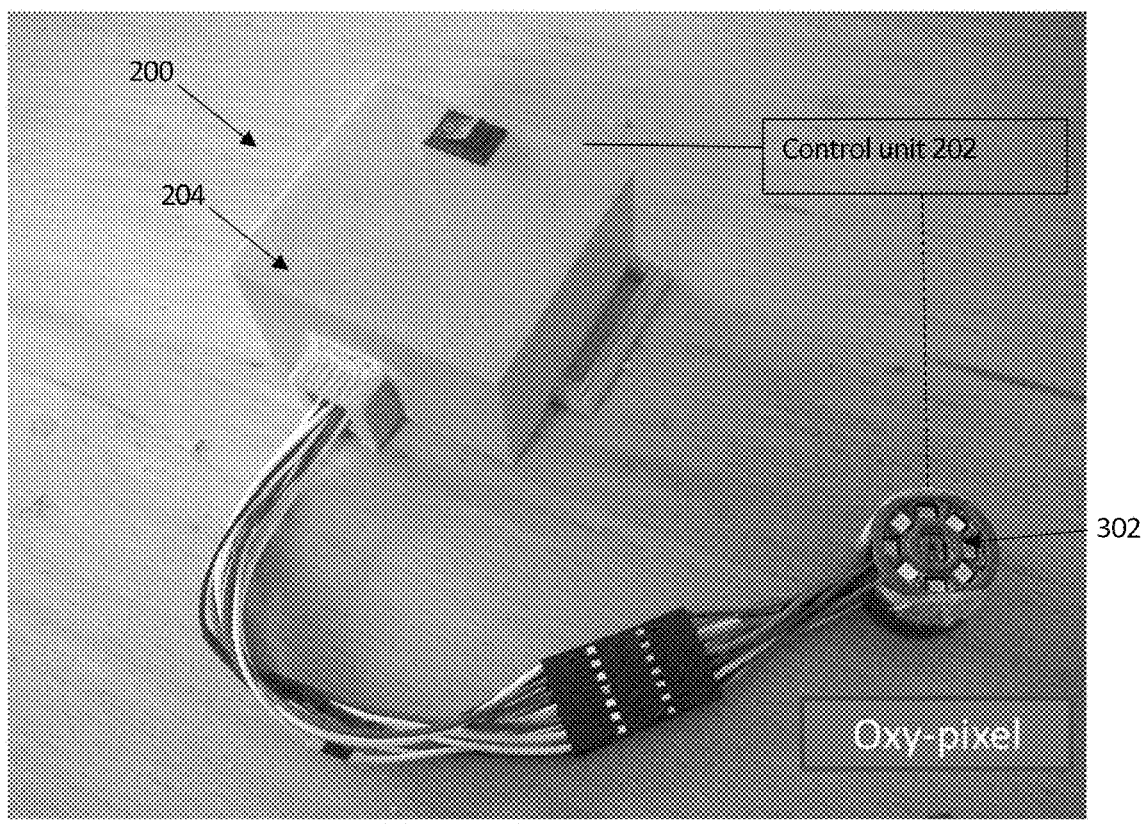
FIG. 4 is a picture illustrating an example of a system for monitoring oxygenation in biological tissue according to some embodiments of the presently disclosed subject matter.

Reference is made to FIG. 4 showing an example of a system 200 of the presently disclosed subject matter. In this specific and non-limiting example, control unit 202 is in data communication with a detector unit 204 being in this example an RGB sensor and with the illumination source 302. In this specific and non-limiting example, illumination source 302 includes three blue LEDs and three white LEDs.

Figure 5A:
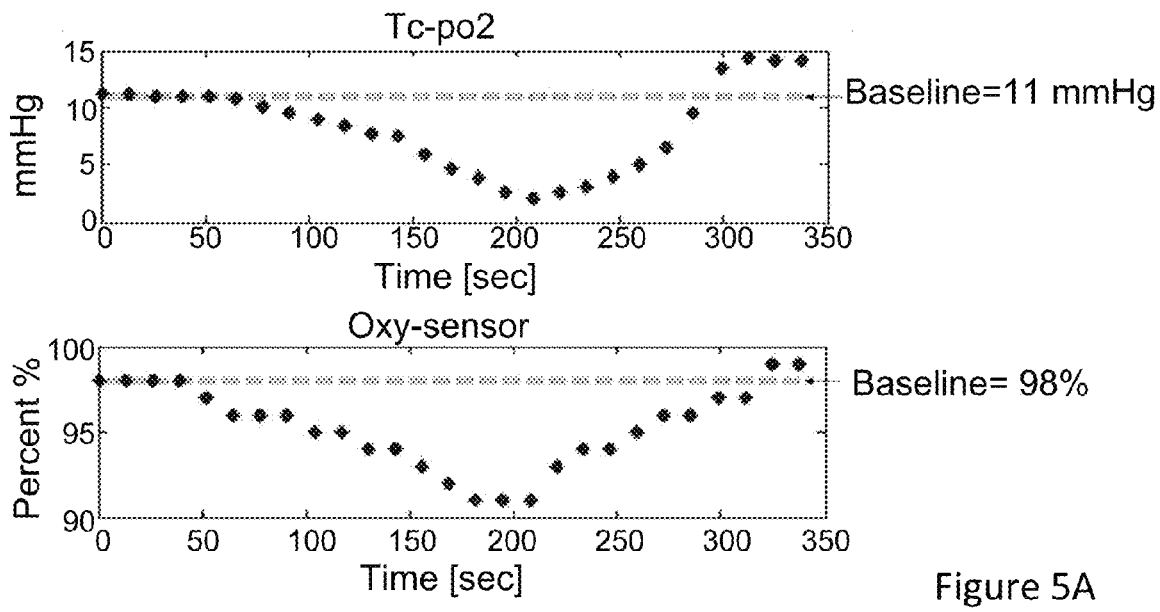
FIG. 5A is a graphical illustration of tissue oxygen saturation ($StO_2$) monitoring using a standard TC-PO2 system (PERIMED) and the technique of the presently disclosed subject matter before and during blood flow occlusion procedure.

Reference is made to FIGS. 5A-5D showing clinical studies performed by using the teachings of the presently disclosed subject matter. The clinical study was aimed at validating the technique of the presently disclosed subject matter versus systemic monitoring of StO2 in a finger by standard a standard pulse oxymeter and tcpO2 devices. In the study, vascular occlusion was performed with a pneumatic cuff causing simultaneous decrease of StO2 in the finger as well as in the skin of the arm. With reference to FIG. 5A, the inflatable cuff was inflated to reduce the flow of oxygenated blood to the forearm, and after 3 minutes the inflatable sleeve was deflated. FIG. 5A shows a correlation between Standard TC-PO2 system (PERIMED) and simultaneous measurements performed using the system of the presently disclosed subject matter. The two devices were placed on patient left arm. Measurements were carried out before, during and after blood circulation reduction by blood-pressure cuff inflation. In FIG. 5A it is seen that the reduction of the blood flow to the arm by inflation of the cuff led to a measureable reduction of the amount of oxygenated blood in the arm. Importantly, the close correlation between the absolute values of the measurements achieved using the teachings herein (lower graph) and tcpO2 (upper graph) demonstrate that the teachings herein can be calibrated (e.g., against a tcpO2 sensor) to provide a quantitative measure of oxygenation status in the biological tissue.

Figure 5B:
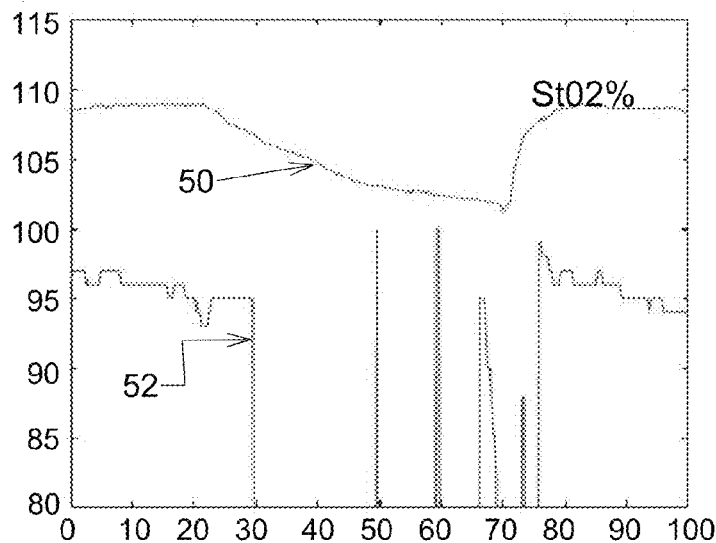
FIGS. 5B-5D are three graphical illustrations of monitoring of tissue oxygen saturation ($StO_2$) by using a conventional pulse oxymeter and the technique of the presently disclosed subject matter before and during blood flow occlusion procedure.
Figure 5C:
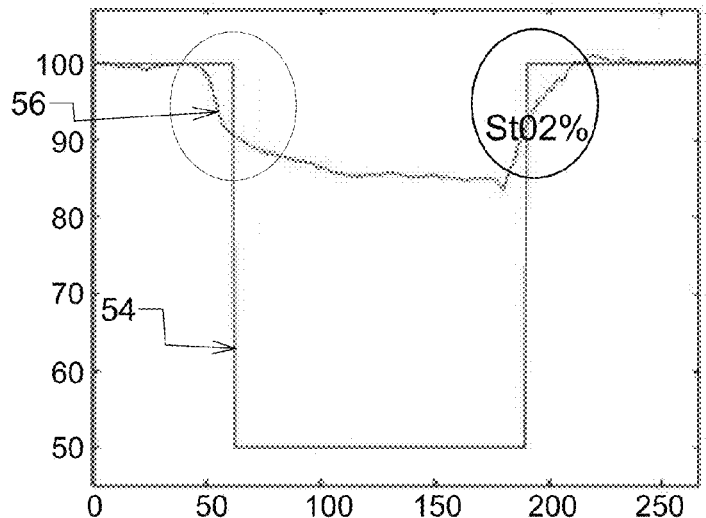
Figure 5D:
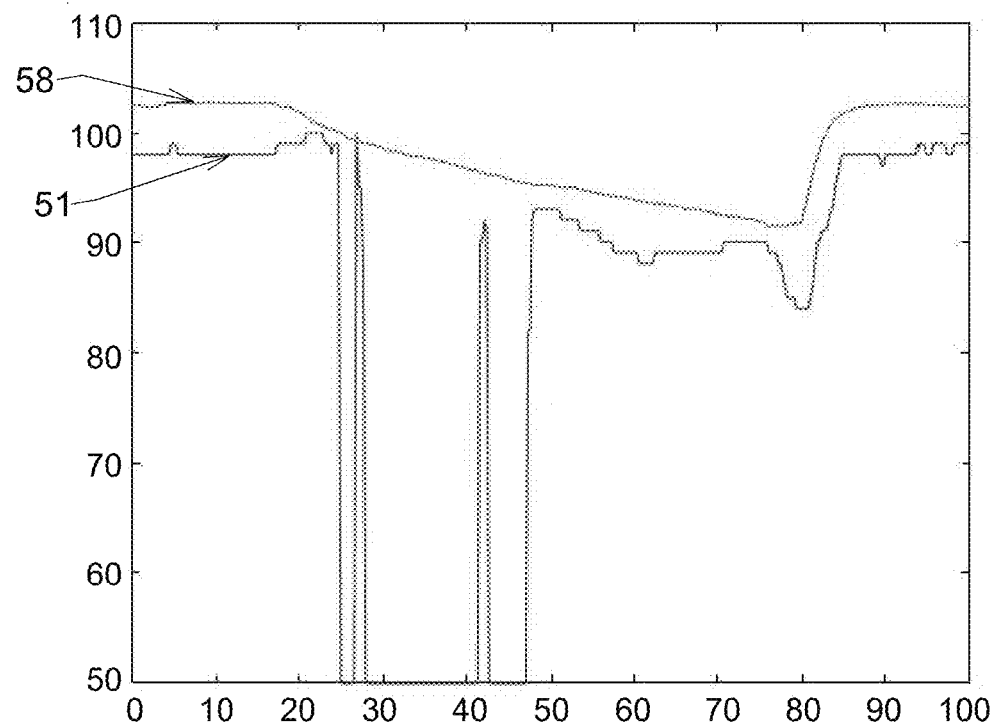

FIGS. 5B-5D show the monitoring of tissue oxygenation in 3 healthy volunteers during vascular occlusion made by a pneumatic cuff inflation. Simultaneous measurements using the teachings of the presently disclosed subject matter and standard pulse oxymeter (finger probe) were compared. More specifically, FIG. 5B shows not calibrated measurements of tissue oxygenation in the arm skin using the system of the presently disclosed subject matter and in the finger using pulse oxymeter during procedure of blood circulation closure by the blood pressure (BP) cuff. No signal from the pulse oxymeter is observed when the pulse is inattentive. FIGS. 5C and 5D show calibrated measurements of tissue oxygenation status in the arm skin using the system of the presently disclosed subject matter and in the finger using pulse oxymeter during procedure of blood circulation closure by the BP cuff. No signal from the pulse oxymeter is observed when the pulse is inattentive. A good correlation between both data at start and at the end of measurements is shown. With reference to FIGS. 5B-5D, it is seen that as long as there was no pulse, the pulse oxymeter could not determine the oxygenated blood content (curves 51, 52, 54), but the tissue-oxygenation sensor according to the teachings herein continued operating without interruption (curves 50, 56, 58). The difference in dynamics between systemic and local tissue oxygen saturation is clearly shown.

Reliable and repeatable results with significant correlation were observed between the system of the presently disclosed subject matter and standard pulse oxymeter measurements in clinical study on volunteers and patients suffering from lung insufficiency. Patients hospitalized in the burns unit can usually suffer from lung insufficiency and acute respiratory failure and undergo mechanical ventilation. Patients can need lung cleaning by fluid suction (a method of removing mucous from the lungs). During this procedure a patient is gradually detached from the respiratory machine and systemic $StO_2$, depending on the extent of lung damage. A number of measurements in patients were carried out using the system of the presently disclosed subject matter simultaneously with systemic $StO_2$ recording by a standard pulse oxymeter during the lung cleaning procedure. The detector unit of the system of the presently disclosed subject matter was attached to the skin of the patient's leg. Monitoring of tissue oxygenation in a patient in the burns unit was carried out using the system of the presently disclosed subject matter and a pulse oxymeter during the procedure of lung cleaning.

Figure 6:
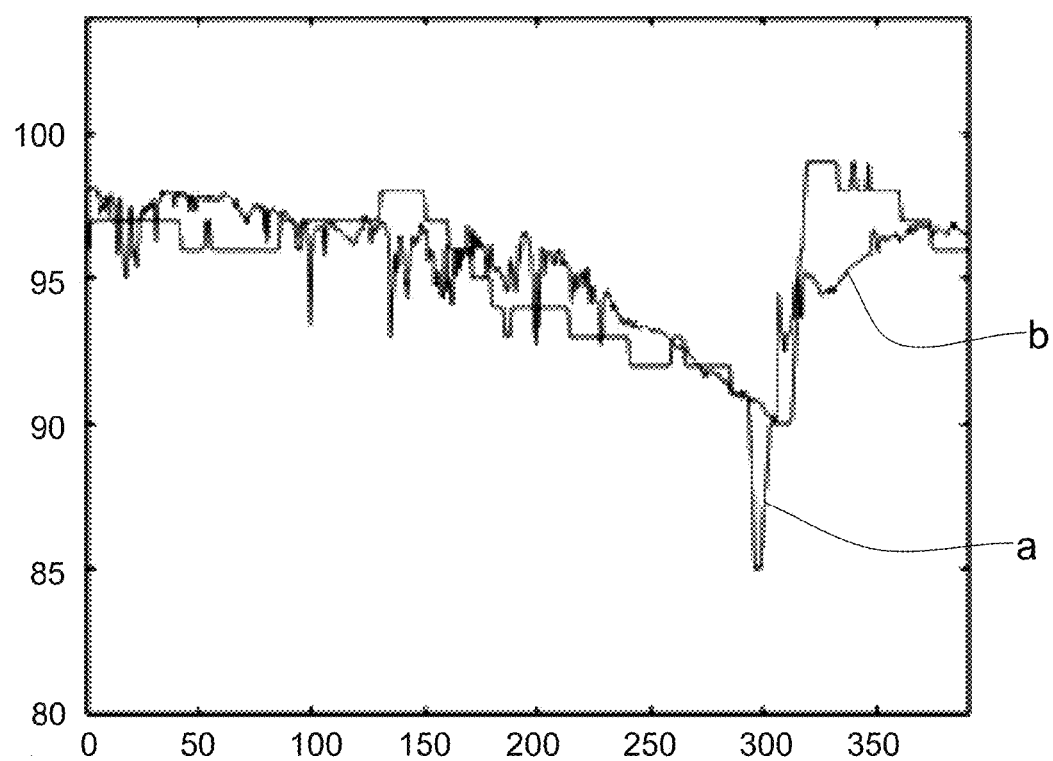
FIG. 6 is a graph representation comparing the content of oxygenated blood in tissue determined by a blood oxygenation sensor according to the teachings herein and commercially available related art devices for determining blood oxygenation, measured during the lung cleaning procedure while being placed on the arm of a severe burn victim who suffered, as a result of burn wounds, from lung insufficiency.

In this connection, reference is made to FIG. 6 which shows the monitoring of tissue oxygenation in a patient in the burns unit, using the system utilizing the tissue-oxygenation sensor of the presently disclosed subject matter in 508 and pulse oxymeter in 510 during the procedure of lung cleaning. The tissue-oxygenation sensor of some embodiments and the pulse oxymeter were placed on the arm of a severe burn victim who suffered from lung insufficiency. In the figure, measurements of tissue oxygenation in a patient of burn department using the system of the presently disclosed subject matter (b) and pulse oxymeter (a) during procedure of lung cleaning are shown. More specifically, trace 'a' corresponds to the values of blood oxygenation determined by the pulse oxymeter, and trace 'b' corresponds to the absolute values of the measurements according to the teachings of some embodiments. As can be seen, there is good correlation between both data at start and at the end of measurements. This demonstrates that the teachings of some embodiments can be calibrated (e.g., against a pulse oxymeter) to provide a quantitative measure of blood-oxygenation status in tissue. Interestingly, the trace started when oxygen supply to the burn victim was suspended, so that the victim breathed normal air, and thus that the oxygenated blood content of the victim fell. Both sensors showed an immediate increase of oxygenated blood content at 300 seconds when the victim was again provided with oxygen to breathe.

Figure 7A:
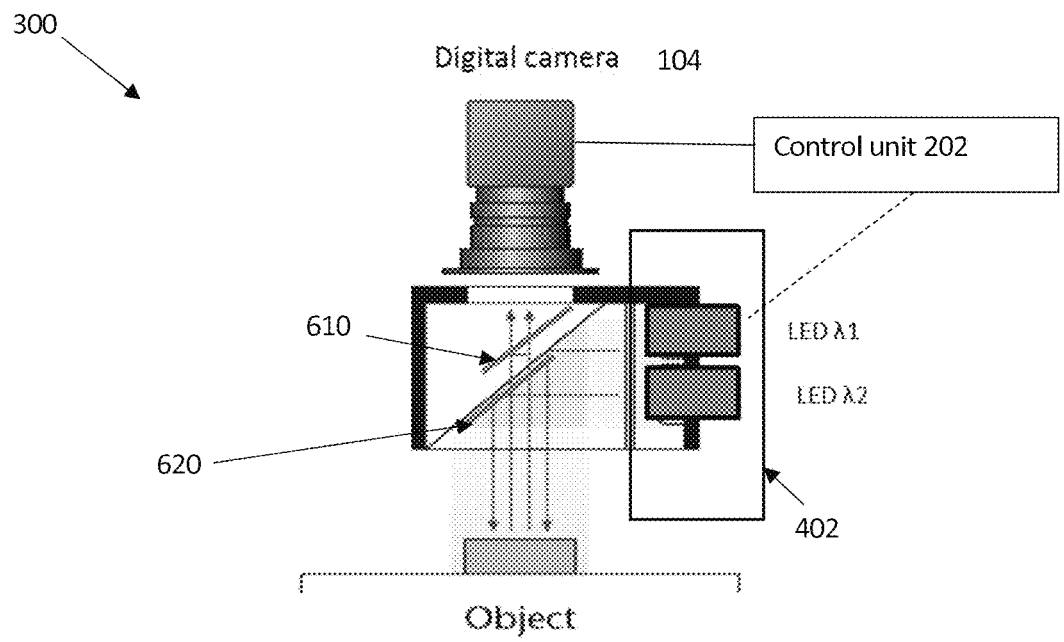
FIGS. 7A-7E are schematic block diagrams showing possible optical imaging set-ups for monitoring oxygenation in biological tissue according to some embodiments of the presently disclosed subject matter.

Reference is made to FIG. 7A representing a possible optical set-up of the system 300 of the presently disclosed subject matter. Control unit 202 is in data communication with a detector unit 104 and with the illumination source 402. In this specific and non-limiting example illumination source 402 includes two narrowband light sources e.g. LEDs or lasers. Each LED illuminates the object at a different selected wavelengths $\lambda_1$ and $\lambda_2$. Detector unit 104 (e.g. digital camera) is used to collect the light response of the tissue being measured/monitored. In this non-limiting example, detector unit 104 includes a single light detector (e.g. a photosensor, a monochrome digital camera, a monochrome digital video camera) that functions as both a first wavelength light detector and a second wavelength light detector. Different beam splitters 610 and 620 are used in system 300 to separate the illumination and the collection of the different wavelengths $\lambda_1$ and $\lambda_2$.

It should be understood that, alternatively or additionally, the same light source (e.g. LED or laser) can be used (e.g. which may be equipped with one or more appropriate spectral filters) to perform two or more measurement sessions with the first and second wavelengths of first and second different but spectrally close wavelength ranges (e.g. being both in the blue spectrum). In this case, the measurements/imaging with two different wavelengths may be implanted in a timely separated sessions. This embodiment will be described more specifically further below.

Figure 7B:
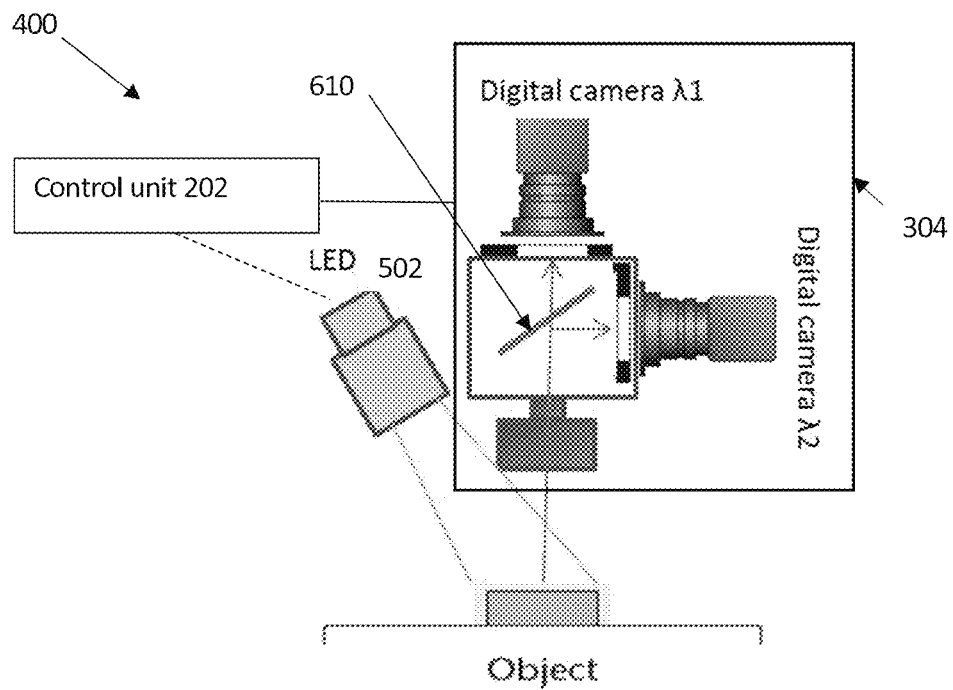

Reference is made to FIG. 7B representing a possible optical set-up of the system 400 of the presently disclosed subject matter. Control unit 202 is in data communication with a detector unit 304 and with the illumination source 502. In this specific and non-limiting example illumination source 502 includes one light source, e.g. LED. A detector unit 104 (e.g. digital camera) includes two detectors to collect the light response. Each detector is configured and operable to collect the light response at the two selected separate wavelengths $\lambda_1$ and $\lambda_2$. A beam splitter 610 is used in system 400 to separate collection of the different wavelengths $\lambda_1$ and $\lambda_2$.

Figure 7C:
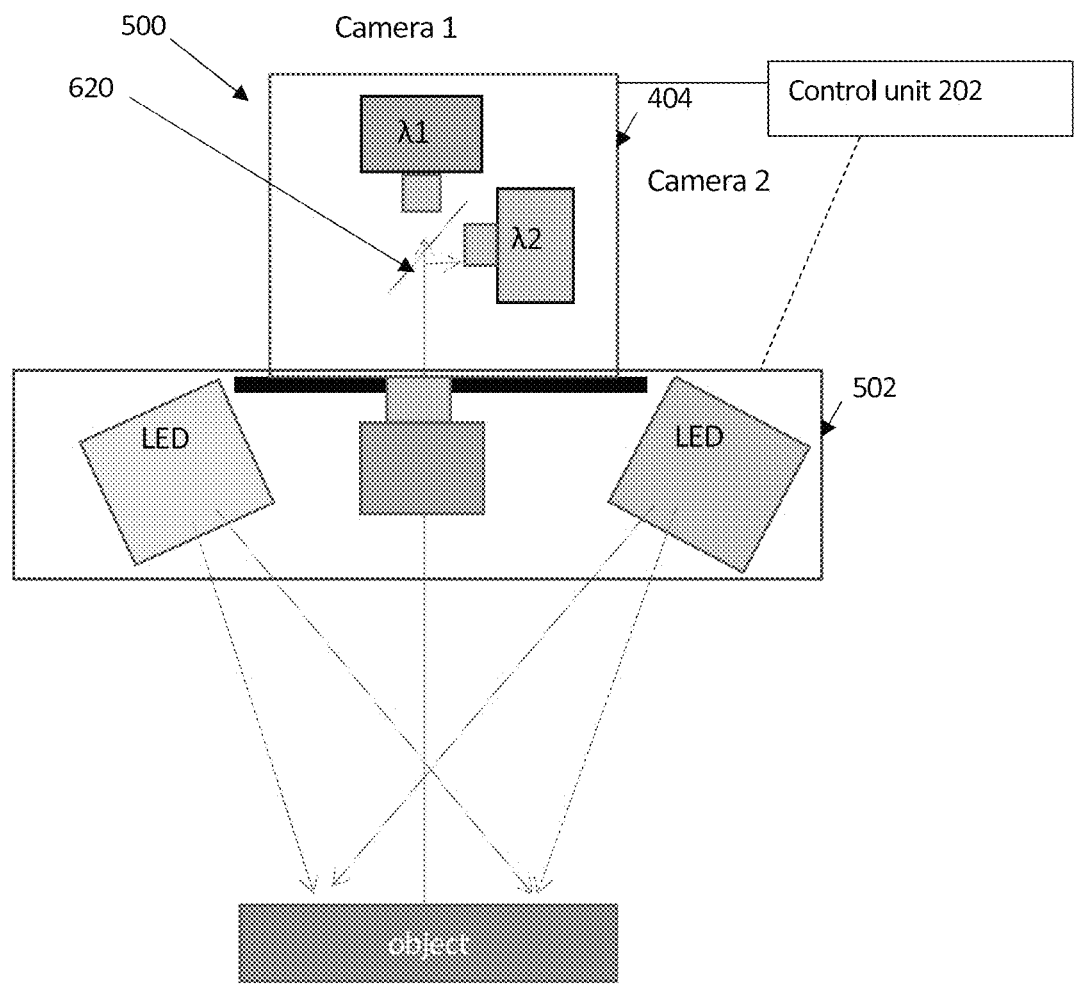

Reference is made to FIG. 7C representing a possible optical set-up of the system 500 of the presently disclosed subject matter. Control unit 202 is in data communication with a detector unit 404 and with the illumination source 502. In this specific and non-limiting example illumination source 502 includes two light sources e.g. LEDs. Each LED illuminates the object at different selected wavelengths $\lambda_1$ and $\lambda_2$. Detector unit 404 (e.g. a digital camera) includes two detectors to collect the light response. Each detector is configured and operable to collect the light response at the two selected separate wavelengths $\lambda_1$ and $\lambda_2$. Beam splitter 620 is used in system 500 to separate the collection of the different wavelengths $\lambda_1$ and $\lambda_2$.

Figure 7D:
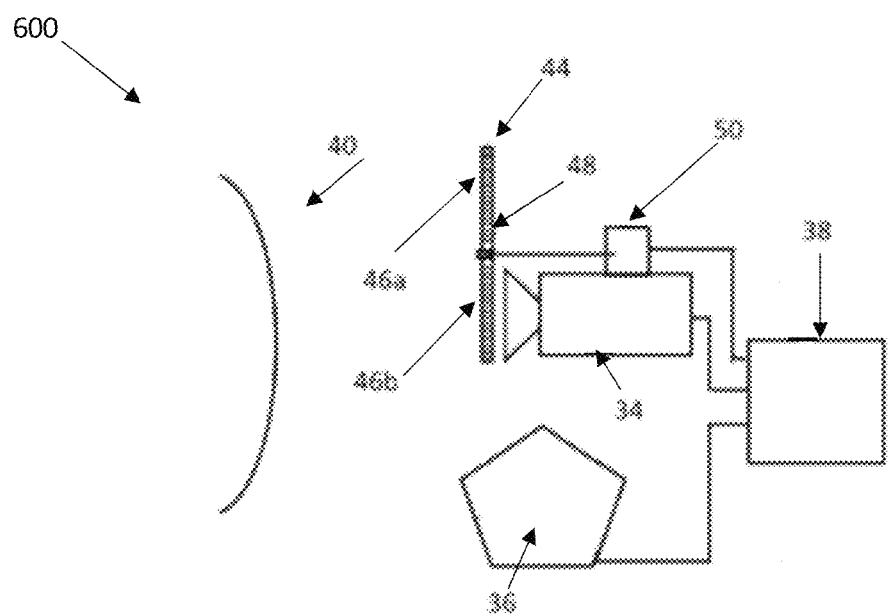

Reference is made to FIG. 7D representing a possible optical set-up of the system 600 of the presently disclosed subject matter. In some embodiments of system 600, illumination source 36 includes a broadband component light source (e.g., a Xenon lamp) for emitting light having both wavelengths in the first range of wavelengths and in the second range of wavelengths. Light emitted by the light source is directed towards a surface 40 of biological tissue through a changeable optical filter 44 that includes a first optical filter 46a that allows transmission only of light having wavelengths in the first range of wavelengths and a second optical filter 46b that allows transmission only of light having wavelengths in the second range of wavelengths. Optical filters 46a and 46b are mounted on a rotatable disk 48. Control unit 38 may activate an electrical motor 50 to rotate disk 48 so that optical filters 46a and 46b alternatingly filter the light from broadband component light source so that a surface of biological tissue 40 is alternatingly illuminated with either exclusively light having wavelengths in the first range, or light having wavelengths in the second range.

In some embodiments, illumination source 102 may include at least two light sources, each light source being configured and operable to illuminate the biological tissue at a different selected wavelength range. The tissue may be illuminated by using alternatively two light beams having different wavelength ranges. Alternatively, the tissue is illuminated by using a broadband light source with two different filters allowing transmission of selected wavelength ranges. For example, the illumination source includes a broadband component light source (e.g., a Xenon lamp) with a functionally-associated changeable optical filter that includes an optical filter that allows transmission only of light having wavelengths in the first range of wavelengths and a different optical filter that allows transmission only light having wavelengths in the second range of wavelengths, for example, mounted on a rotatable disk.

Figure 7E:
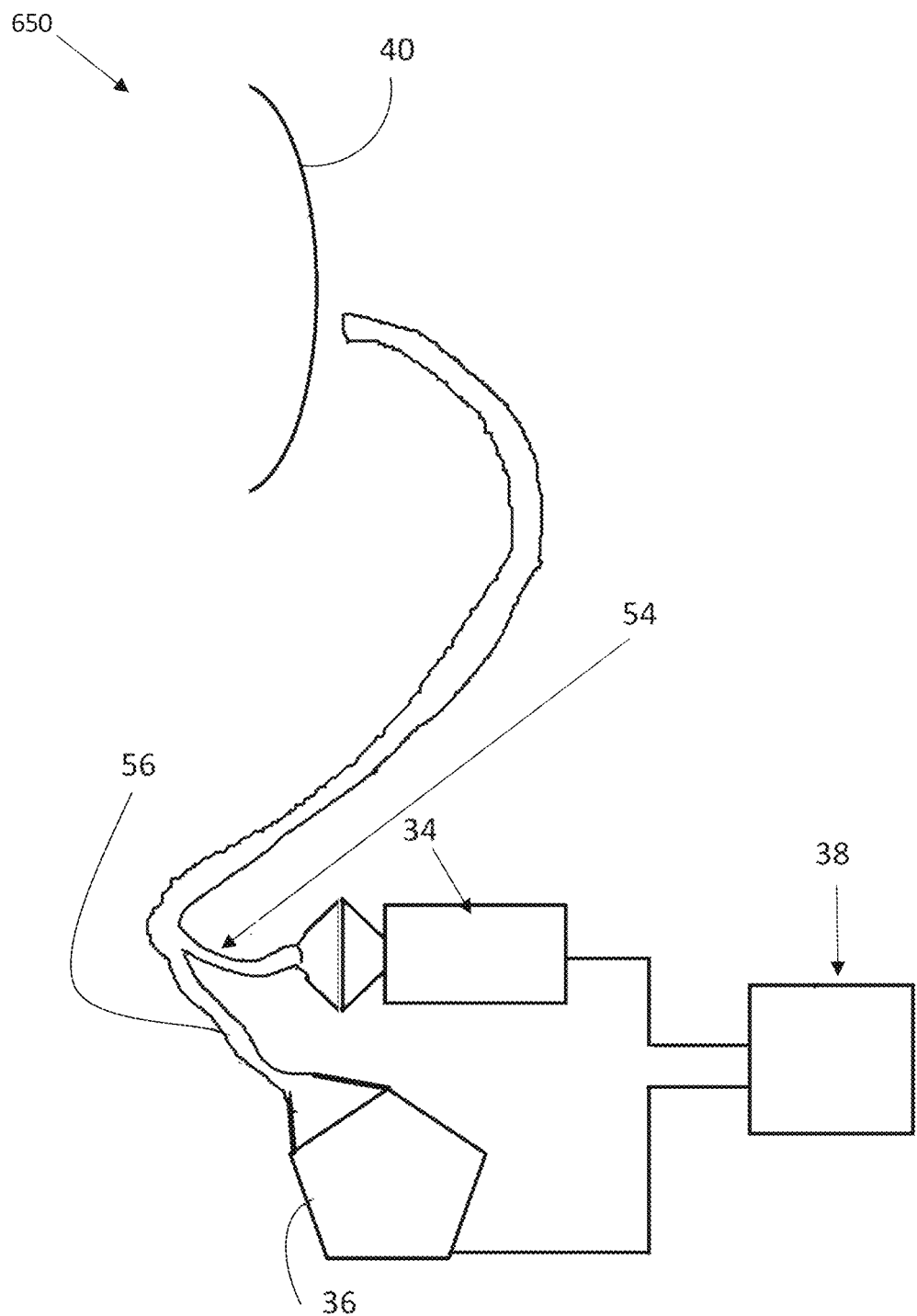

Reference is made to FIG. 7E representing a possible optical set-up of the system 650 of the presently disclosed subject matter. System 650 includes two optical light guides (optical fiber cables): optical light guide 54 for guiding the light response from the surface 40 of biological tissue to a light detector 34 and optical light guide 56 for guiding illumination light from the illumination source 36 to illuminate the surface 40 of biological tissue.

Figure 8:
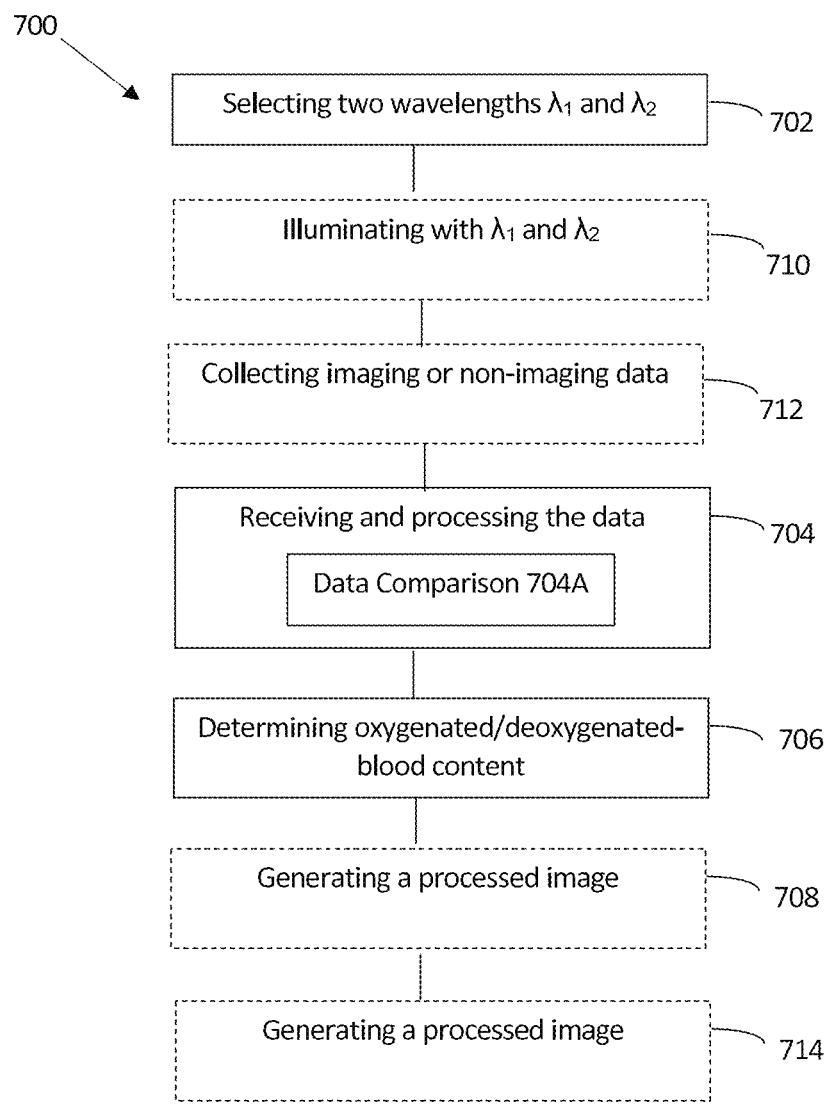
FIG. 8 is a flow chart illustrating an example of a method for monitoring oxygenation in biological tissue.

Reference is made to FIG. 8, showing a flow chart 700 illustrating the methods of the presently disclosed subject matter.

Method 700 includes in 702 determining operational data for use in one or more measurement sessions (i.e. illumination and/or collection wavelengths) to enable collection of data indicative of oxygenated/deoxygenated tissue status of the biological tissue. This is done by selecting two separate wavelengths in two wavelength ranges to enable generation of data indicative of light responses of one region of the biological tissue to the two wavelengths. These two wavelength ranges include a first wavelength range in which the absorbance of the deoxyhemoglobin within the tissue is higher than the oxyhemoglobin, and a second wavelength range in which the absorbance of the oxyhemoglobin within the tissue is higher than the deoxyhemoglobin, or vice versa, and the two wavelengths in the two wavelength ranges include first and second wavelengths satisfying a condition of a relatively high ratio (preferably substantially/approximately highest ratio) between the absorbance of the deoxyhemoglobin and the oxyhemoglobin for the identified wavelength ranges. The method, in steps 704 and 706, performs analysis of the light response data measured in the one or more measurement sessions using the above two wavelengths. The measured data can be received from a measured data provider device which may be the measurement/imaging unit itself (online mode) or a storage device where the measured data has been previously (off line mode). Thus, the measured data indicative of a light response from the same region of a biological tissue at two separate selected wavelength ranges is received and processed and an oxygenated/deoxygenated tissue status of the biological tissue is determined.

In some embodiments, the processing in 704 includes comparing data indicative of each selected wavelength range in 704A. If a non-imaging data is received, the comparison may be implemented by calculating a ratio between two averaged intensities being indicative of the light response from the same region of biological tissue at the two separate selected wavelength ranges. Alternatively, if imaging data is received, the comparison may be implemented by identifying in each image, pixels being indicative of a specific area of the region; and performing pixel-by-pixel comparison of the at least two pixelated images for each specific area. Alternatively, if spectral imaging data is received, the comparison may be implemented by extracting from the at least two pixelated images, at least two monochrome images corresponding to the selected wavelength ranges of illumination and/or collection respectively; and performing pixel-by-pixel comparison of each specific area of the at least two monochrome images.

In some embodiments, method 700 includes in 708 generating a processed image being indicative of tissue oxygenation/deoxygenation mapping. The processed image of the tissue is indicative of oxygenation status at the surface of the tissue in comparison with oxygenation status in the depth of the tissue. In some embodiment, method 700 includes in 708 generating a processed image being indicative of oxygenation status of first and second tissue portions both located in a vicinity of the surface of the tissue being monitored.

In some embodiments, method 700 includes in 710 illuminating biological tissue with at least two electromagnetic beams having different selected wavelength ranges $\lambda_1$ and $\lambda_2$.

In some embodiments, method 700 includes in 712 collecting imaging or non-imaging data being indicative of a light response from the same region of biological tissue at two separate selected wavelength ranges.

In some embodiments, method 700 includes in 714 displaying an oxygenation/deoxygenation status of the region of interest.

In some such embodiments, the method further includes: during determining of the intensity of light diffusely reflected from the least one area of the surface of biological tissue in the first range of wavelengths, illuminating the at least one area with light having wavelengths in the first range of wavelengths; and during determining of the intensity of light diffusely reflected from the least one area of the surface of biological tissue in the second range of wavelengths, illuminating the at least one area with light having wavelengths in the second range of wavelengths.

For example, in some embodiments the method is performed with a control unit 202 that is part of a pen-like tissue oxygenation probe that is used to assist medical personnel to determine whether or not a portion of tissue is receiving sufficient oxygenated blood. Medical personnel make contact of the probe with the surface of tissue, e.g., a transplanted flap, and activate the system of the presently disclosed subject matter. The system reports whether or not the processing provides evidence that the flap has a sufficient oxygenated blood content to be considered viable.

The monitoring may be performed repeatedly for any suitable period of time. For example, if the teachings herein are implemented for video imaging of blood-oxygenation status of tissue during surgery, the period of time is for as long as the medical personnel deem it useful, typically for the duration of the surgery. For example, if the teachings herein are implemented for the continuous monitoring of blood-oxygenation status of a tissue flap of a person in a recovery ward, the period of time is for as long as the medical personnel deem it useful, typically for a period of a few days until medical personnel deem that blood supply to the flap is sufficient and no longer needs monitoring. In particular to the teaching of some embodiments monitoring of tissue oxygenation status at the surface of the tissue may be provided quantitatively and continuously, independently of systemic blood circulation status conventionally provided by pulse oximetry.

The repetition rate can be any suitable rate as determined for each specific embodiment by what is useful for medical personnel. Since the amount of data gathered and processed is very low, the rate can be 100 Hz, or even more frequently, if this is found to be useful. In some embodiments slower rates are sufficient, for example, in some embodiments where the teachings herein are implemented for monitoring of blood-oxygenation of a tissue flap of a person in a recovery ward, the rate of repetition is typically not faster than 1 Hz, for example, once a minute or even once every 5 minutes.

Figure 9A:
FIGS. 9A-9C are three images acquired by using the technique of the presently disclosed subject matter of a finger under three different clamping modes: normal (FIG. 9A), Ischemia of two minutes (FIG. 9B) and after re-perfusion (FIG. 9C)
Figure 9B:
Figure 9C:

Reference is made to FIGS. 9A-9C showing three images acquired by using the technique of the presently disclosed subject matter of a finger under three different clamping modes: normal (FIG. 9A), Ischemia of two minutes (FIG. 9B) and after re-perfusion (FIG. 9C). FIG. 9A shows a tissue ischemia model by finger clamping under normal finger conditions. In this specific and non-limiting example, the finger was illuminated by using a broad band light source (cold white) with simultaneous acquisition at blue light (21) and red (22) wavelength ranges. The image processing includes a gray scale image conversion to false color image using 16-color LUT.

EXAMPLES

Example 1A

Figure 10:
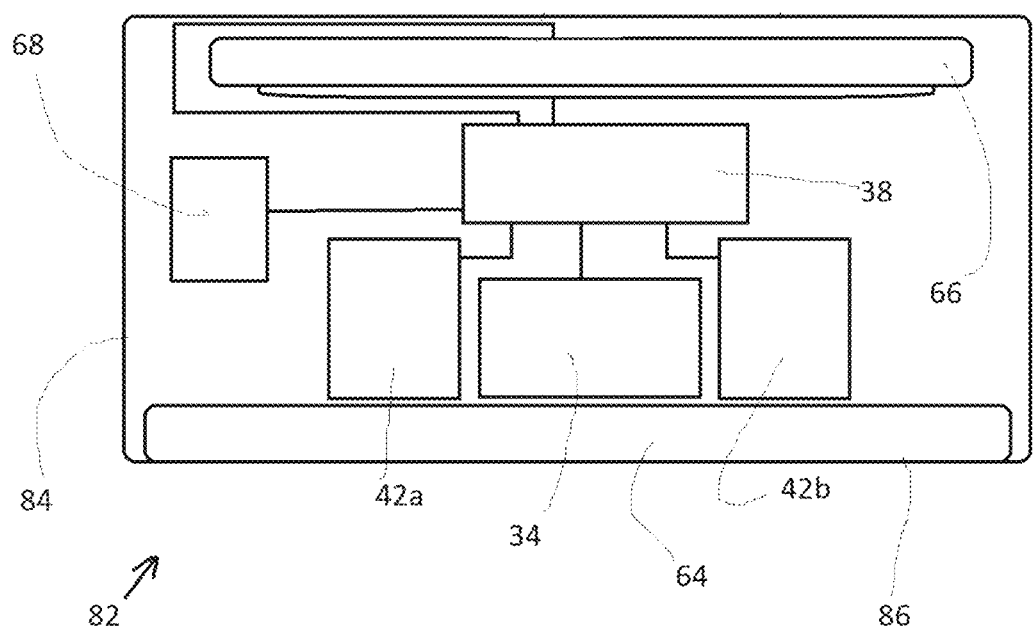
FIG. 10 is a schematic block diagram showing a possible optical set-up for monitoring oxygenation in biological tissue according to some embodiments of the presently disclosed subject matter.

For monitoring the oxygenated-blood tissue status of a flap of tissue, the system includes two oxygenation sensors 82 schematically depicted in FIG. 10. Each oxygenation sensor 82 has a sealed waterproof sensor body 84 with a contact surface 86 having a 0.5 mm radius illumination window 64 transparent to wavelengths of light in a range of at least 405 nm to 670 nm.

Contained inside sensor body 84 are the following:
a. a power source 66 (battery) for supplying electrical power to the other components of the oxygenation sensor;
b. as a first illuminator 42a, an LED configured to produce light having wavelengths from 405 nm to 420 nm and projecting the produced light through illumination window 64;
c. as a second illuminator 42b, an LED configured to produce light having wavelengths from 630 nm to 670 nm and projecting the produced light through illumination window 64;
d. as a first (blue) and second (red) detector, a single photodetector 34 configured to determine the intensity of light in a range of at least 405 nm to 670 nm;
e. a Bluetooth® wireless transceiver 68; and
f. a controller 38 including a computer processor, a timer and solid state memory on a printed circuit board functionally associated with the other components of the oxygenation sensor and configured to:
 i. receive activation commands sent by a user via transceiver 68;
 ii. on receipt of a command, to alternately activate the first and second illuminators 42a and 42b to illuminate an area of a surface of biological tissue which surface 86 contacts at a rate and for a duration received from user via transceiver 68;
 iii. to receive and store on the memory of controller 38 from photodetector 34 Ifirst (the intensity of light diffusely scattered from the surface of the biological tissue when the first illuminator 42a is activated) and Isecond (the intensity of light diffusely scattered from the surface of the biological tissue when the second illuminator 42b is activated);
 iv. comparing received Ifirst and Isecond by calculating Ioxy=Isecond/Ifirst; and
 v. transmitting via wireless transceiver 68 a calculated Ioxy at a user-selected rate to a remote device with which the oxygenation sensor 82 is in wireless communication via the wireless transceiver 68. Oxygenation sensor 68 is devoid of any lens.

For convenient use, the first of two provided oxygenation sensors 82 is affixed with an adhesive applied to the frame of contact surface 86 to an earlobe of a human subject. The second of the two provided oxygenation sensors 82 is affixed with an adhesive applied to the frame of contact surface 86 to a flap of tissue the human subject, the flap having being formed during flap surgery.

A Bluetooth® piconet is formed including a Bluetooth®-enabled smartphone as the master and the two oxygenation sensors 86 as slaves, the smartphone programmed as may be necessary to implement the teachings herein. At a rate of once a second, the smartphone receives Ioxy(reference) from the earlobe sensor 86 and Ioxy(flap) from the flap sensor 86.

For the first minute after the piconet is formed, the smartphone calculates the ratio OxContent(0)=Ioxy(flap)/Ioxy(reference) as the reference value that indicates that the flap receives sufficient oxygenated blood from the blood supply that remained and/or was newly made during the flap surgery.

Subsequently, the two oxygenation sensors transmit the two Ioxy values and the smartphone calculates the corresponding OxContent(t) value. As long as OxContent(t) remains within 80% of OxContent(0), the smartphone simply stores OxContent(0) in the smartphone memory. If OxContent(t) drops below 80% of OxContent(0), the smartphone transmits an alarm to a resident physician who then can choose to examine whether or not the flap is still viable.

Turning back to FIGS. 7A-7C schematically exemplifying the optical system suitable to implement the presently disclosed subject matter, it should be noted that first and second different wavelengths may be relatively close. Also, the light source may utilize laser(s). In other words, considering for example the set-up of FIG. 6A, the elements marked LED $\lambda_1$ and LED $\lambda_2$ can constitute two different lasers, or alternatively, two successive operations, respectively, of the same laser. Accordingly, the control unit (202 in FIG. 6A) may be configured and operable to process first image data and second image data corresponding to/collected in timely separated imaging sessions. This may be implemented for example by illuminating the tissue with the first wavelength (e.g. using the first illumination source) in a first time window and illuminating the same tissue with the second wavelength (e.g. using the second illumination source) in second time window. Operating with alternating data (i.e. performing imaging sessions in timely separated measurement/imaging sessions) while using different illumination wavelengths eliminates a need for spectral selective filters 610, 620 that may for example be replaced by cross polarizers. Thus the reference numbers 610, 620 in the figure may constitute polarizers. Alternatively, the same illumination source with different first and second spectral filters operated in the first and second time windows, respectively, can be used. A further advantage of using such alternating measurement mode is that illumination in different but close wavelengths can be performed without interference between the collected signals. Cross polarizers 610, 620 if used may be configured to filter out specular reflection from the tissue surface and therefore would provide high signal to background ratio. It should also be noted that a laser unit producing polarized light may be used, which configuration provides higher energy efficiency when used in conjunction with cross polarization schemes. Further, the use of different but close wavelengths advantageously allows for eliminating a need to compensate for chromatic aberrations.

More specifically, in such embodiments utilizing illumination with different but spectrally close first and second wavelengths, the wavelengths may be of about 415 nm (415±5 nm) and about 430-440 nm (e.g. 435 nm). It should be noted that, since the back scattered light signal is practically from the same depth in the tissue, the imaging system does not need any optics to compensate for depth difference, and alternating between measurements with the different wavelengths would be simplified. Diode lasers for such embodiment are readily available and may also be controlled to provide short pulses to reduce energy consumption and increase safety. Thus, the use of such light sources of close spectral proximity may be readily available and may provide for the monitoring of tissue oxygenation separately and independently from large blood vessel oxygenation information. It should be emphasized that tissue oxygenation information collected in such manner is independent of large blood vessels oxygenation information because blue light is predominantly reflected and scattered from the surface and at immediate proximity to the surface of the tissue, whereas large blood vessels are present at the depth of the tissue.

Example 1B

Identical to Example 1A where the monitored surface is:
transplanted tissue (e.g., a big toe transplanted as a thumb);
a flap from the forehead used to reconstruct a nose;
a breast reconstructed from abdominal tissue;
a breast subsequent to breast reduction surgery; and
a portion of a person who has been in an accident and it is not clear whether the portion is viable or not.

Example 1C

A tissue oxygenation sensor similar to that described in Example 1A was used. The body of the sensor was a 2-cm diameter plastic disk. An RGB photosensor (S9706 by Hamamatsu Photonics K.K., Shizuoka, Japan) was placed in the center of the disk. The photosensor was found to detect the intensity of red light at 650 nm and of blue light at 413 nm. In a circle, around the photosensor, eight LEDs were placed as an illumination source of the sensor: four warm white LEDs (ASMT-UWB-1-NX3J2 by Broadcom Ltd., Irvine, California, USA) and four blue LEDs (OCU-400 411 OS by Osa Opto Light GmbH, Berlin, Germany that were found to produce 413 nm light).

A standard inflatable cuff was placed on the upper arm of a patient. The tissue-oxygenation sensor and a standard commercially-available tcpO2 sensor (Perimed AB, Järfälla, Sweden) were placed close together on the underside of the forearm of the patient where the output terminals of the two sensors was directed to a laptop computer to receive and analyze the data received from the two sensors: from the tcpO2 sensor the measure of blood oxygenation was indicated in units of mm Hg, and from the tissue-oxygenation sensor as Isecond/Ifirst. The results of this experiment are shown in FIG. 5A described above.

It should be noted that similar high-correlation measurement results between the tissue-oxygenation sensor of some embodiments and the standard pulse oxymeter have been obtained and are shown in FIGS. 5B-5D and FIG. 6, described above. These figures show the close correlation between the values of blood oxygenation determined by the standard pulse oxymeter and the absolute values of the measurements using the tissue-oxygenation sensor of some embodiments.

Example 2A

Figure 11:
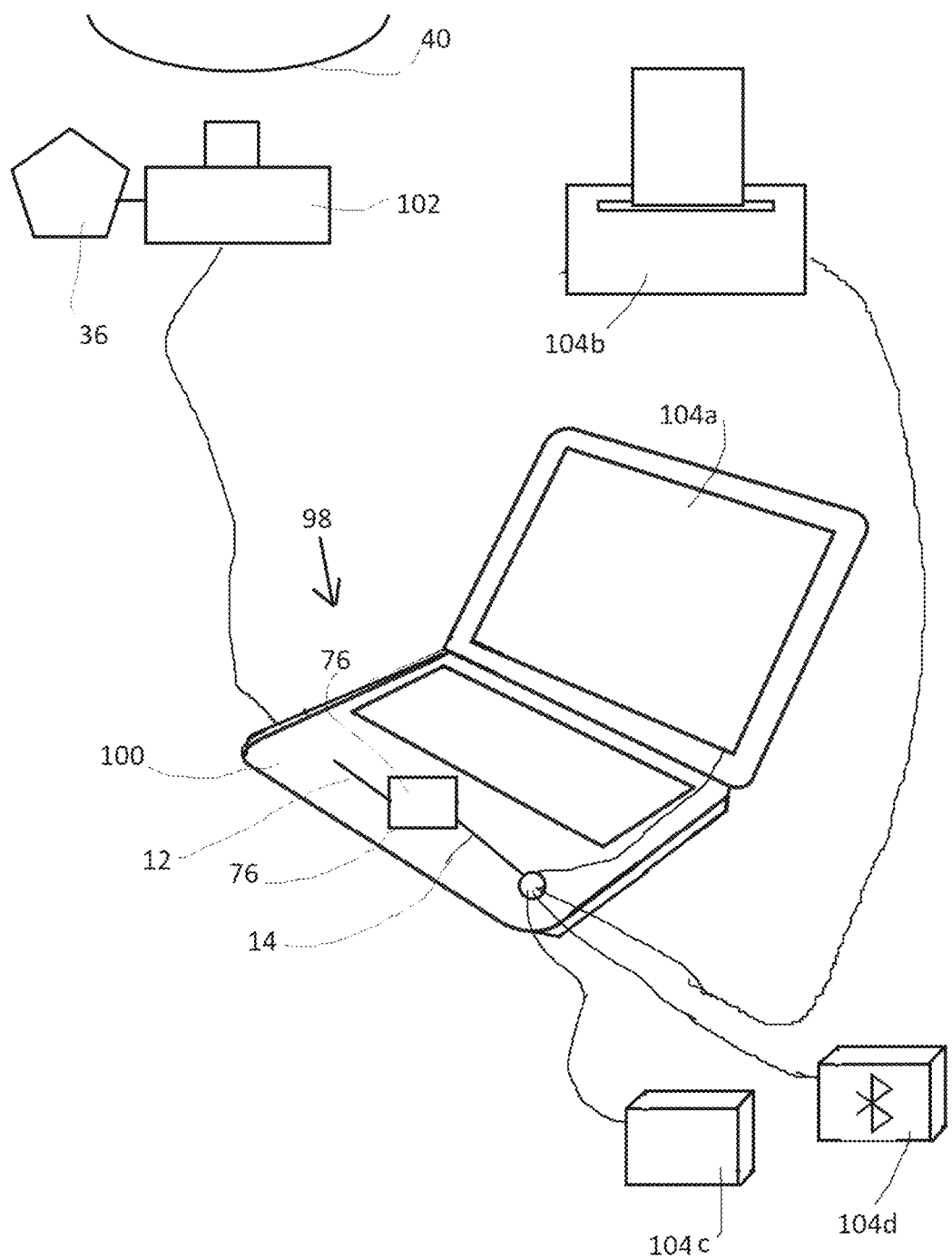
FIG. 11 schematically depicts an embodiment of a device which includes a computer processor functionally-associated with a spectral imaging camera.

In FIG. 11, an embodiment of a system 98 according to the teachings herein is schematically depicted, substantially a computer processor 76 that was a component of a commercially-available laptop computer 100. Through an input port 12, computer processor 76 was functionally associated with a spectral imaging camera 102 and a broadband illumination source 36 (a commercially-available SD-300 spectral imaging camera from ASI (Migdal Haemek, Israel) fitted with a halogen lamp illumination source and a cross-polarizing filter set). Processor 76 was also functionally associated through an evidence output port 14 with output components: as display components a display screen 104a and a printer 104b, as a storage component an external hard disk 104c as a storage component and as a transmission component a Bluetooth® transceiver 104d.

The image-processing software associated with camera 102, was programmed to run on computer 100 to automatically extract from an acquired spectral image received from camera 102 a first pixelated monochrome image data (blue image data) and a second pixelated monochrome image data (red image data) according to the teachings herein, and then to automatically generate a third pixelated monochrome image data as a tissue oxygenation map data according to the teachings herein using pixel-by-pixel division (for each pixel, Ioxy=Isecond/Ifirst).

Using the set-up described in FIG. 11, a spectral image of the surface of a body part is obtained and automatically a blood-oxygenation tissue status map data of the body part is generated, showing the status of oxygenation in the tissue under the surface of that body part.

Specifically, a patient placed a clamp around the base of a finger, then generated a third pixelated monochrome image data as a blood-oxygenation tissue status map by acquiring a spectral image of the finger using camera 102 and providing the acquired spectral image to processor 76 as described above, once every 30 seconds. A corresponding blood-oxygenation tissue status map data was generated, saved on hard disk 104c and a colorized version was displayed on screen 104a and optionally printed on paper using printer 104b. If required, the blood-oxygenation tissue status map data was transmitted to a smartphone using transceiver 104d.

The displayed blood-oxygenation tissue status maps were colorized in false color using freely-available software implementing 16-color LUT (Lookup Table) as known in the related art of digital photography so that pixels having the highest values were displayed as dark red (qualitatively indicating more oxygenated blood in the tissue underlying the skin corresponding to that pixel) and pixels having the lowest values were displayed as dark blue (qualitatively indicating less oxygenated blood in the tissue underlying the skin corresponding to that pixel). Intermediate intensity values were assigned one of 14 distinct colors that progressed from dark red progressing to orange, orange progressing to yellow, yellow progressing to green, green progressing to blue and ultimately to dark blue.

From the displayed colorized blood-oxygenation tissue status maps it was seen how the oxygenated-blood content in the finger was progressively reduced. After three minutes, the clamp was removed from the finger and it was seen from the displayed colorized blood-oxygenation tissue status maps how the amount of oxygenated-blood in the finger progressively increased back to normal.

Example 2B

The system was used to simultaneously acquire blue image data and red image data of a human retina. The pair of simultaneously-acquired images, blue image data from a first camera and red image data from a second camera, was input into an appropriately-configured (using image processing software) general purpose laptop computer as a processor to perform pixel-by-pixel division of the red image data by the blue image data (for each pixel, Ioxy=Isecond/Ifirst) to generate third pixelated monochrome image data constituting a blood-oxygenation tissue status map data of the retina. The computer output the third pixelated monochrome image data by displaying the data as a greyscale image on the computer screen and by saving the data on the computer hard disk.

The displayed greyscale image was processed and the intensity values associated with portions of the image that clearly corresponded to arteries, veins and to the retina, were identified. A colorized third image was generated in false color using freely-available software implementing 16-color LUT (Lookup Table) as known in the art of digital photography so that pixels having the higher Ioxy values associated with the identified arteries were displayed as red (qualitatively indicating more oxygenated blood in the tissue underlying the retinal surface corresponding to that pixel), pixels having intermediate Ioxy values associated with the identified veins were displayed as blue (qualitatively indicating less oxygenated blood in the tissue underlying the retinal surface corresponding to that pixel), and pixels having low Ioxy values associated with the identified nervous and connective tissue devoid of blood were displayed as white (qualitatively indicating the lack of any blood in the tissue underlying the retinal surface corresponding to that pixel).

The resulting angiographic image not only showed exceptionally high resolution, showing even the smallest arteries and veins, but allowed a person studying the image to clearly differentiate between arteries and veins.

Example 2C

In some embodiments, an optical wave guide (e.g., an optical wave guide that is part of an endoscope) is connected to an objective lens of an imaging camera (e.g. a spectral camera) so that the optical wave guide guides light reflected from a surface of biological tissue to the objective lens to be detected. In some such embodiments, the tip of an endoscope includes an illumination source, e.g., a source of white light. In alternate such embodiments, an optical wave guide is functionally associated with the illumination source (e.g., a white light source, a Xenon lamp) such that the illumination source guides light from the illumination source, to illuminate the surface of biological tissue.

Example 2D

A physician is caring for a subject having a foot ulcer as a result of diabetes. In a manner similar or identical to the described above, blue image data and red image data of the foot ulcer are acquired, and blood-oxygenation tissue status map data of the foot ulcer is generated. The physician prescribes treatment of the patient with a vasodilator. After a week of the patient taking the vasodilator, blue image data and red image data of the foot ulcer are acquired, and blood-oxygenation tissue status map data of the post-treatment foot ulcer is generated as described above. The physician visually displays and compares the two blood-oxygenation tissue status map data to see whether or not the treatment with the vasodilator was effective in treating the ulcer.

Example 2E

The teachings herein were used to monitor skin flap viability after a number of surgical procedures. In the surgical procedures, a subject with a flap of tissue (the flap formed during flap surgery) or a graft was monitored, while the patient was in hospital. In a manner similar or identical to the described above, blue image data and red image data were acquired, and blood-oxygenation tissue status map data of the flap and surrounding tissue was generated as required where blue image data wavelengths were 405 nm to 420 nm, and red image data wavelengths were 630 nm to 670 nm and P3(i)=P1(i)/P2(i). The generated blood-oxygenation tissue status map data was output by storing in a digital memory, e.g. a solid state hard disk. The generated blood-oxygenation tissue status map data was displayed and viewed to ascertain whether the flap/graft had sufficient blood supply to be viable, or required surgical intervention. In a first instance, a common rodent flap model in experimental surgery was used to create the dorsal based fasciocutaneous flap in a mouse by partial tissue dissection. FIGS. 12A (RGB image) and 12B (blood-oxygenation tissue status map generated from a spectral image) are of the flap of skin, one hour after the operation. FIGS. 12C (RGB image) and 12D (blood-oxygenation tissue status map generated from a spectral image) are of the same flap of skin 72 hours after the operation, showing necrosis resulting from insufficient blood supply to the bottom portion of the flap.

In a second instance, the results of a forehead to nose transposition were monitored in a patient. In such surgery, a skin flap from the forehead is moved over to the nose while still receiving blood from an artery in the forehead. When and if the skin flap develops sufficient blood supply from the tissue in the region of the nose, the forehead artery can be disconnected from the skin flap.

FIG. 13A depicts a blood-oxygenation tissue status map generated from a spectral image of the skin flap 3 days after surgery. In the upper right side of the image is seen a surgical clamp that is used to stop blood flowing from the forehead artery to the skin flap. The dark color of the skin flap (indicated by the black arrow) shows that the flap has insufficient oxygenated blood from the nose area and relies on blood from the forehead artery to remain viable.

FIG. 13B depicts an analogous blood-oxygenation tissue status map generated from a spectral image of the skin flap 10 days after surgery. The white color of the skin flap shows that the blood supply to the flap from the nose area is sufficient to ensure viability of the flap and that the forehead artery can be safely disconnected from the skin flap.

In a third instance, the results of nose reconstruction surgery 14 days after the nose reconstruction surgery was performed were evaluated using an embodiment of the teachings herein. FIG. 14A shows a complete image of the patient's face. FIG. 14B shows a blood-oxygenation tissue status map generated from the spectral image. The dark color of the reconstructed nose in the blood-oxygenation tissue status map of FIG. 14B shows that the reconstructed nose had sufficient blood supply to be viable. The above experiments are repeated where the blue image data is of wavelengths from 460 nm to 480 nm and the red image data is of wavelengths 630 nm to 670 nm. The results obtained are substantially identical to those described above.

Example 2F

In a manner similar or identical to the described above, blue image data and red image data were acquired, of damaged extremities and organs of a person who had undergone a vehicular accident, and a corresponding blood-oxygenation tissue status map data was generated. The blood-oxygenation tissue status map data was output by displaying on a screen (optionally colorized) and optionally by saving, for example, on a hard disk. A treating physician studied the displayed blood-oxygenation tissue status map data to determine which tissue could be saved, for example by surgery, and which had to be excised.

Example 2G

The teachings herein were used for real-time monitoring of brain function during stimulation. An imaging system similar to that described above was provided, where the digital cameras were video cameras and the associated processor was configured to continuously simultaneously acquire pairs of red image data (wavelengths 630 nm to 670 nm) and blue image data (wavelengths 405 nm to 420 nm) from the respective cameras at a desired rate (e.g., 1 Hz, 20 Hz, 60 Hz) according to the teachings herein, in real time, to generate a corresponding blood-oxygenation tissue status map data using pixel-by-pixel division (Ioxy=Isecond/Ifirst), and then to output the generated blood-oxygenation tissue status map data by saving to a disk and by displaying a real-time video blood-oxygenation tissue status map of a surface of biological tissue from which the images were acquired.

During brain surgery on a subject, pairs of image data were acquired of exposed cortical surface of the right hemisphere of the brain of subject, and the real-time video blood-oxygenation tissue status map of a surface of the cerebral cortex, were displayed on a screen visible to the performing surgeon. When the surgeon stimulated an extremity of the subject (e.g., a left hand), a portion of the cortical surface with a higher oxygenated blood content as a result of the stimulation indicated that the portion of the cortical surface was related to the stimulated extremity.

FIG. 15A depicts an RGB image of a portion of a right hemisphere of a human subject's brain. FIGS. 15B, 15C and 15D depict blood-oxygenation tissue status maps of the portion of the cortical surface generated according to the teachings herein where: FIG. 15B is with no stimulation, FIG. 15C is with low stimulation and FIG. 15D is with high stimulation of a left hand. FIG. 15C and FIG. 15D indicate a portion of the brain that showed increased oxygenated blood content as a result of the stimulation. The above experiment was repeated where the blue image data is of wavelengths from 460 nm to 480 nm and the red image data is of wavelengths 630 nm to 670 nm. The results obtained were substantially identical to those described above.

Example 2H

Figure 16A:
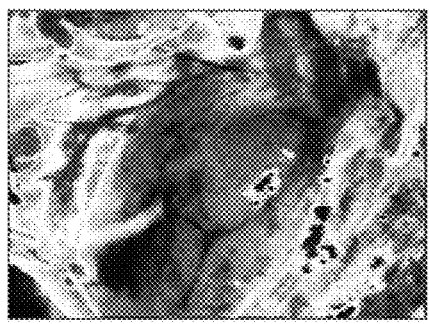
FIGS. 16A-16C show the teachings herein used for monitoring the treatment of cancer using photothermal treatment.
Figure 16B:
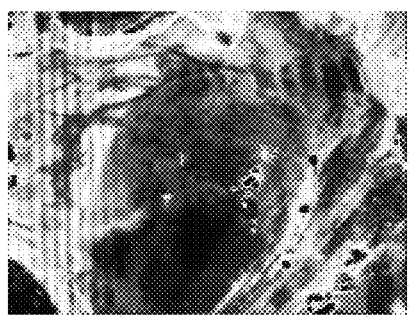
Figure 16C:
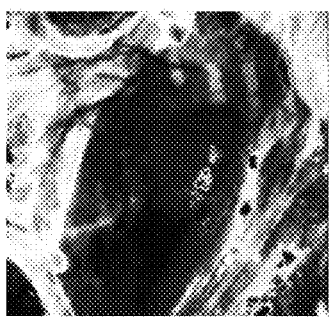

The teachings herein were used for monitoring the treatment of cancer using photothermal treatment. A nude mouse was innoculated subcutaneously with H29 human colon carcinoma. After three weeks, the tumor was exposed and underwent photothermal treatment using an IPL (intense pulsed light) device by ESC Medical Systems (Yokneam, Israel) substantially as described in Kostenich G et al "Photothermic treatment of pigmented B16 melanoma using a broadband pulsed light delivery system" in Cancer Letters, 157, 2, (161), (2000). During the treatment, full spectral image data of the tumor were acquired using a spectral imaging camera. Blue image data with wavelengths from 460 nm to 480 nm and red image data with wavelengths 630 nm to 670 nm were extracted from the full spectral image data. Blood-oxygenation tissue status maps as described herein were generated by pixel-by-pixel division (P3(i)=P1(i)/P2(i). FIG. 16A depicts the generated blood-oxygenation tissue status map of the tumor before photothermal treatment. It is seen that the tumor is undamaged. FIG. 16B depicts the generated blood-oxygenation tissue status map of the tumor after being subjected to a number of light pulses corresponding to 40 J/cm$^2$. The reduction of oxygenated blood at the bottom of the tumor indicates vascular occlusion and ischemia caused by light irradiation. FIG. 16C depicts the generated blood-oxygenation tissue status map of the tumor after being subjected to a number of light pulses corresponding to 80 J/cm$^2$. The complete absence of oxygenated blood over the entire tumor indicates that substantially all the tumor blood vessels were occluded by irradiation with the light, resulting in death of the tumor cells. The above experiment was repeated where the blue image data with wavelengths from 405 mm to 420 mm and the red image data with wavelengths 630 mm to 670 mm were extracted from the full spectral image data. The results obtained were substantially identical to those described above.

The invention claimed is:

1. A system for monitoring oxygenation in biological tissue, the system comprising a control unit being configured and operable to receive data being indicative of light response from the same region of the biological tissue being subjected to illumination and collection at two separate wavelengths in two selected wavelength ranges and processing the data by comparing data indicative of each selected wavelength range to determine an oxygenated/deoxygenated status of the biological tissue, wherein the two wavelength ranges of illumination and collection comprise a first wavelength range in which the absorbance of the deoxyhemoglobin within the tissue is higher than the oxyhemoglobin, and a second wavelength range in which the absorbance of the oxyhemoglobin within the tissue is higher than the deoxyhemoglobin or vice versa, and the two wavelengths in said two wavelength ranges comprise first and second wavelengths satisfying a predetermined condition of a ratio between the absorbance of the deoxyhemoglobin and the oxyhemoglobin for each of the first and second identified wavelengths;

the first wavelength of a pair of the first and second wavelengths of concurrent illumination of the biological tissues and the collection of the light response is selected from the group consisting of: 410 nm, 412 nm, 415 nm, 418 nm, and 420 nm, the second wavelength of a pair of the first and second wavelengths of the concurrent illumination of the biological tissues and the collection of the light response is selected from the group consisting of: 600 nm, 630 nm, 640 nm, 650 nm 660 nm, 670 nm, and 800.

2. The system of claim 1, wherein said predetermined condition corresponds to maximal or highest ratio between the absorbance of the deoxyhemoglobin and the oxyhemoglobin for each of the first and second identified wavelengths.

3. The system of claim 1, wherein the first wavelength range or the second wavelength range are selected as follows: (i) the first wavelength range is selected such that the data is indicative of a first tissue portion located at the surface of the tissue being monitored, while the second wavelength range is selected such that the data is indicative of a second tissue portion located in a second tissue portion at the depth of the tissue being monitored or (ii) wherein the first and second wavelength ranges are substantially in the same spectral band, the first and second wavelength ranges being selected such that the data is indicative of a surface tissue portion of the tissue being monitored.

4. The system of claim 1, wherein the first and second wavelengths of concurrent illumination of the biological tissues and the collection of the light response are 415 nm and 650 nm, respectively.

5. The system of claim 1, wherein said control unit is configured and operable to at least one of
   (i) process the data by calculating a ratio between two averaged intensities being indicative of a light response from the same region of a biological tissue being illuminated and collected at the two separate selected wavelength ranges;
   (ii) determine the oxygenated/deoxygenated status of the biological tissue in real-time or
   (iii) generate a processed image of the tissue being monitored, said processed image being indicative of oxygenation tissue status at the surface of the tissue coupled to oxygenation tissue status in the depth of the biological tissue.

6. The system of claim 1, wherein the data comprises at least two pixelated images; the processing of the data comprises identifying, in each image, pixels being indicative of a specific area of the region; performing pixel-by-pixel comparison of the at least two pixelated images for each specific area; determining an oxygenated/deoxygenated status of the biological tissue per pixel, and generating a processed image being indicative of tissue oxygenation/deoxygenation tissue status mapping.

7. The system of claim 1, further comprising at least one of (i) a detector unit being configured and operable to collect the light response or (ii) an illumination source being configured and operable to illuminate the biological tissue with the two separate wavelength ranges of electromagnetic beams or (iii) at least two cross polarizing elements being associated with the illumination source and an imager unit being configured and operable to filter out specular reflection from the tissue.

8. The system of claim 7, wherein said detector unit comprises at least one of (i) an imager unit being configured and operable to receive the light response and to generate at least two pixelated images thereof or (ii) a non-imaging photodetector unit being configured and operable to receive the light response of the same region from the biological tissue being illuminated and collected at the two separate selected wavelength ranges, and to generate at least two averaged intensities of the region thereof.

9. The system of claim 8, wherein said imager unit comprises at least one of (i) a spectral imager being configured and operable to receive the light response and to generate at least two pixelated spectral images thereof or (ii) at least two imagers, each imager being configured and operable to detect at least one electromagnetic beam in a different selected wavelength range.

10. The system of claim 9, wherein the data comprises at least two pixelated spectral images; the processing of the data comprises extracting from the at least two pixelated spectral images, at least two monochrome images corresponding to the selected wavelength ranges of illumination and collection respectively, performing pixel-by-pixel comparison for each specific area of the at least two monochrome images and generating a processed image being indicative of a spectrally-resolved tissue oxygenation/deoxygenation mapping.

11. The system of claim 7, wherein said control unit is configured and operable to control the illumination source and to select the wavelength ranges of illumination.

12. The system of claim 7, wherein said illumination source comprises at least two light sources, each light source being configured and operable to illuminate the biological tissue at a different selected wavelength range.

13. A method for use in monitoring oxygenation in a biological tissue, the method comprising determining operational data for use in one or more measurement sessions to enable collection of data indicative of oxygenated/deoxygenated tissue status of the biological tissue, said determining comprising:
   selecting two separate wavelengths in two different wavelength ranges, respectively, for use in said one or more measurement sessions to enable generation of data indicative of light responses of one region of the biological tissue to said two wavelengths, wherein the two wavelength ranges comprise a first wavelength range in which the absorbance of the deoxyhemoglobin within the tissue is higher than the oxyhemoglobin and a second wavelength range in which the absorbance of the oxyhemoglobin within the tissue is higher than the deoxyhemoglobin or vice versa, and said two wavelengths comprise first and second wavelengths from said first and second wavelength ranges, satisfying a predetermined condition of a ratio between the absorbance of the deoxyhemoglobin and the oxyhemoglobin for each of the first and second wavelengths;
   the first wavelength of a pair of the first and second wavelengths of concurrent illumination of the biological tissues and the collection of the light response is selected from the group consisting of: 410 nm, 412 nm, 415 nm, 418 nm, and 420 nm, the second wavelength of a pair of the first and second wavelengths of the concurrent illumination of the biological tissues and the collection of the light response is selected from the group consisting of: 600 nm, 630 nm, 640 nm, 650 nm 660 nm, 670 nm, and 800.

14. The method of claim 13, wherein said predetermined condition corresponds to the highest ratio between the absorbance of the deoxyhemoglobin and the oxyhemoglobin for each of the first and second wavelengths.

15. The method of claim 13, wherein the first and second wavelengths of concurrent illumination of the biological tissues and the collection of the light response are 415 nm and 650 nm, respectively.

16. The method of claim 13, wherein the first and second wavelength ranges are substantially in the same spectral band, the first and second wavelength ranges being selected such that the data is indicative of a surface tissue portion of the tissue being monitored.

17. The method of claim 13, further comprising at least one of (i) performing said one or more measurement sessions using two light responses corresponding to said two wavelengths and determining an oxygenated/deoxygenated-tissue status of the biological tissue (ii) reducing specular reflection from the tissue; (iii) illuminating the biological tissue with at least two electromagnetic beams having different selected wavelength ranges; (iv) collecting imaging or non-imaging data being indicative of a light response from the same region of a biological tissue at two separate selected wavelength ranges or (v) displaying an oxygenation/deoxygenation status of the region of interest.

18. The method of claim 17, wherein determining an oxygenated/deoxygenated-tissue status of the biological tissue per pixel is performed in real-time.

19. The method of claim 17, wherein the data comprises at least one of (i) at least two pixelated images; the processing of the data comprises identifying in each image, pixels being indicative of a specific area of the region; performing pixel-by-pixel comparison of the at least two pixelated images for each specific area; determining an oxygenated/deoxygenated status of the biological tissue per pixel, and generating a processed image being indicative of a tissue oxygenation/deoxygenation mapping; (ii) at least two spectral pixelated images; the processing of the data comprises extracting from the at least two pixelated images, at least two monochrome images corresponding to the selected wavelength ranges of illumination and collection respectively; performing pixel-by-pixel comparison of each specific area of the at least two monochrome images; and generating a spectrally-resolved image and processed false color image being indicative of oxygenation tissue status or (iii) non-imaging data being indicative of at least two averaged intensities at the two separated wavelengths ranges, and processing of the data comprises calculating a ratio between the two averaged intensities.

20. The method of claim 19, comprising generating a processed image of the tissue being indicative of oxygenation status of at least one of: (i) a first tissue portion located at the vicinity of the surface of the tissue being monitored in comparison with oxygenation status of a second tissue portion located in the depth of the tissue; (ii) first and second tissue portions located in a vicinity of the surface of the tissue being monitored.

* * * * *